US007141352B2

(12) United States Patent
Watanabe et al.

(10) Patent No.: US 7,141,352 B2
(45) Date of Patent: Nov. 28, 2006

(54) BASIC COMPOUND, RESIST COMPOSITION AND PATTERNING PROCESS

(75) Inventors: Takeru Watanabe, Niigata-ken (JP); Takeshi Kinsho, Niigata-ken (JP); Koji Hasegawa, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/849,197

(22) Filed: May 20, 2004

(65) Prior Publication Data

US 2005/0008968 A1 Jan. 13, 2005

(30) Foreign Application Priority Data

May 21, 2003 (JP) ............................ 2003-142853

(51) Int. Cl.
*G03F 7/004* (2006.01)
*G03F 7/30* (2006.01)

(52) U.S. Cl. .................. 430/270.1; 430/325; 430/326; 430/330; 430/905; 430/910

(58) Field of Classification Search ............. 430/207.1, 430/921, 920, 325, 326, 330, 905, 910, 270.1
See application file for complete search history.

(56) References Cited

U.S. PATENT DOCUMENTS

| | | | | |
|---|---|---|---|---|
| 5,442,087 | A | 8/1995 | Eichhorn et al. | |
| 5,525,453 | A | 6/1996 | Przybilla et al. | |
| 5,529,886 | A | 6/1996 | Eichhorn et al. | |
| 5,612,169 | A | 3/1997 | Eichhorn et al. | |
| 5,658,706 | A | 8/1997 | Niki et al. | |
| 5,691,100 | A | 11/1997 | Kudo et al. | |
| 5,744,281 | A | 4/1998 | Niki et al. | |
| 5,843,319 | A | 12/1998 | Przybilla et al. | |
| 6,004,724 | A | 12/1999 | Yamato et al. | |
| 6,261,738 | B1 | 7/2001 | Asakura et al. | |
| 6,361,920 | B1 * | 3/2002 | Loccufier et al. | 430/264 |
| 6,703,181 | B1 | 3/2004 | Hayashi et al. | |
| 6,770,419 | B1 * | 8/2004 | Khojasteh et al. | 430/270.1 |
| 2005/0095527 | A1 * | 5/2005 | Yokoyama et al. | 430/270.1 |

FOREIGN PATENT DOCUMENTS

| | | | |
|---|---|---|---|
| JP | 63-27829 | A | 2/1988 |
| JP | 2-27660 | B2 | 6/1990 |
| JP | 5-158239 | A | 6/1993 |
| JP | 5-232706 | A | 9/1993 |
| JP | 5-249662 | A | 9/1993 |
| JP | 5-249683 | A | 9/1993 |
| JP | 5-257282 | A | 10/1993 |
| JP | 5-289322 | A | 11/1993 |
| JP | 5-289340 | A | 11/1993 |
| JP | 6-194834 | A | 7/1994 |
| JP | 6-242605 | A | 9/1994 |
| JP | 6-242606 | A | 9/1994 |
| JP | 6-263716 | A | 9/1994 |
| JP | 6-263717 | A | 9/1994 |
| JP | 6-266100 | A | 9/1994 |
| JP | 6-266111 | A | 9/1994 |
| JP | 7-92678 | A | 4/1995 |
| JP | 7-92680 | A | 4/1995 |
| JP | 7-92681 | A | 4/1995 |
| JP | 7-120929 | A | 5/1995 |
| JP | 7-128859 | A | 5/1995 |
| JP | 7-134419 | A | 5/1995 |
| JP | 9-95479 | A | 4/1997 |
| JP | 9-208554 | A | 8/1997 |
| JP | 9-230588 | A | 9/1997 |
| JP | 2000-314956 | A | 11/2000 |

OTHER PUBLICATIONS

Hinsberg et al., "Fundamental studies of airborne chemical contamination of chemically amplified resists", Journal of Photopolymer Science and Technology, vol. 6, No. 4, 1993, 535-546.

Kumada et al., "Study on over-top coating of positive chemical amplification resists for KrF excimer laser lithography", Journal of Photopolymer Science and Technology, vol. 6, No. 4, 1993, 571-574.

Hatakeyama et al., "Investigation of discrimination enhancement with new modeling for poly-hydroxystyrene positive resists", Journal of Photopolymer Science and Technology, vol. 13, No. 4, 2000, 519-524.

* cited by examiner

*Primary Examiner*—John S. Chu
(74) *Attorney, Agent, or Firm*—Birch, Stewart, Kolasch & Birch, LLP

(57) ABSTRACT

Resist compositions comprising basic compounds having a benzimidazole skeleton and a polar functional group have an excellent resolution and an excellent focus margin and are useful in microfabrication using electron beams or deep-UV light.

6 Claims, No Drawings

BASIC COMPOUND, RESIST COMPOSITION AND PATTERNING PROCESS

This Non-provisional application claims priority under 35 U.S.C. § 119(a) on Patent Application No(s). 2003-142853 filed in Japan on May 21, 2003, the entire contents of which are hereby incorporated by reference.

FIELD OF THE INVENTION

The present invention relates to a novel resist composition suitable for microfabrication technology, and more particularly to a chemical amplification resist composition. It also relates to a patterning process using the resist composition.

BACKGROUND ART

Of the efforts currently being made to achieve a finer pattern rule in the drive for higher integration and operating speeds in LSI devices, deep-ultraviolet lithography is thought to hold particular promise as the next generation in microfabrication technology. Deep-UV lithography is capable of fabrication to dimensions of 0.2 μm or less and, when a resist having low light absorption is used, can form patterns with sidewalls that are nearly perpendicular to the substrate. One technology that has attracted a good deal of attention recently utilizes high-intensity KrF and ArF excimer lasers as the deep-UV light source. This technology is being used in large-volume production, prompting a desire for resists having a low light absorption and a high sensitivity.

Acid-catalyzed, positive-working chemical amplification resists (e.g., JP-B 2-27660 and JP-A 63-27829) developed in response to the above needs are endowed with excellent properties, including a high sensitivity, high resolution and good dry-etching resistance, which make them especially promising as resists for deep-UV lithography.

However, one problem with chemical amplification resists is that, when the standing time from exposure to post exposure bake (PEB) is long, the line pattern formed during patterning acquires a "T-top" shape characterized by widening at the top of the pattern. This defect is called "post exposure delay" (PED). Another problem with such resists is "footing," which is a widening of the resist pattern close to the substrate that occurs on a basic substrate, particularly a silicon nitride or titanium nitride substrate. The T-top effect is believed to result from a decrease in solubility at the surface of the resist film, and the footing effect at the substrate surface appears to arise from a decline in solubility near the substrate. An additional problem is that acid-labile group elimination is a dark reaction which proceeds during the interval between the exposure step and the PEB step, reducing the final dimensions of the pattern lines.

These problems represent major drawbacks to the practical use of chemical amplification resists. Because of such defects, prior-art positive-working chemical amplification resists are difficult to dimensionally control in the lithographic process, and dimensional control is also lost during dry etching of the substrate (see, for example, W. Hinsberg et al., Journal of Photopolymer Science and Technology, Vol. 6, No. 4, 535–546 (1993); and T. Kumada et al., ibid., 571–574).

In positive-working chemical amplification resists, the problems of PED and footing on the substrate surface are believed to be caused in large part by basic compounds which are either airborne or present on the surface of the substrate. The acid at the surface of the resist film that has been generated by exposure reacts with airborne bases and is deactivated. Prolonged standing until post-exposure bake results in a corresponding increase in the amount of deactivated acid, making it more difficult for the acid-labile groups to decompose. A substantially insolubilized layer thus forms at the surface, giving the resist pattern a T-top shape.

It is well-known in the art that the addition of a basic compound can check the influence of airborne bases, and is thus effective also against PED (see, for example, JP-A 5-232706, JP-A 5-249683, JP-A 5-158239, JP-A 5-249662, JP-A 5-257282, JP-A 5-289322, JP-A 5-289340, JP-A 6-194834, JP-A 6-242605, JP-A 6-242606, JP-A 6-263716, JP-A 6-263717, JP-A 6-266100, JP-A 6-266111, JP-A 7-128859, JP-A 7-92678, JP-A 7-92680, JP-A 7-92681, JP-A 7-120929 and JP-A 7-134419).

Familiar basic compounds include nitrogenous compounds such as amine compounds and amide compounds. Specific examples include pyridine, polyvinylpyridine, aniline, N-methylaniline, N,N-dimethylaniline, o-toluidine, m-toluidine, p-toluidine, 2,4-lutidine, quinoline, isoquinoline, formamide, N-methylformamide, N,N-dimethylformamide, acetamide, N-methylacetamide, N,N-dimethylacetamide, 2-pyrrolidone, N-methylpyrrolidone, imidazole, α-picoline, β-picoline, γ-picoline, o-aminobenzoic acid, m-aminobenzoic acid, p-aminobenzoic acid, 1,2-phenylenediamine, 1,3-phenylenediamine, 1,4-phenylenediamine, 2-quinolinecarboxylic acid, 2-amino-4-nitrophenol, and triazine compounds such as 2-(p-chlorophenyl)-4,6-trichloromethyl-S-triazine.

Of these, pyrrolidone, N-methylpyrrolidone, o-aminobenzoic acid, m-aminobenzoic acid, p-aminobenzoic acid and 1,2-phenylenediamine are preferred.

These nitrogenous compounds are weak bases and can alleviate the T-top problem, but such compounds are unable to control the reaction when highly reactive acid-labile groups are used; that is, they cannot control acid diffusion. With the addition of a weak base, the dark reactions in PED in particular proceed in unexposed areas, causing slimming of the line dimensions and a loss of film thickness from the line surface during PED. To overcome such problems, it is desirable to add a strong base.

However, a higher basicity is not necessarily better. For example, good effects cannot be obtained with the addition of the following super-strong bases: DBU (1,8-diazabicyclo[5.4.0]-7-undecene), DBN (1,5-diazabicyclo[4.3.0]-5-nonene), 1,8-bis(dimethylamino)naphthalene or quaternary ammonium hydroxides such as tetramethylammonium hydroxide.

The addition of a base having an excellent generated acid capturing effect works well to increase the contrast and thereby achieve a high resolution. The dissociation constants of the acid and base within water can be explained in terms of pKa, but the acid capturing ability within the resist film is not directly related to the pKa of the base. This is discussed by Hatakeyama et al. in Journal of Photopolymer Science and Technology, Vol. 13, No. 4, pp. 519–524 (2000).

SUMMARY OF THE INVENTION

It is therefore an object of the invention to provide a resist composition which has a high resist film thickness loss preventing effect, and also has a high resolution and a good focus margin widening effect. Another object of the invention is to provide a patterning method which uses the resist composition. A further object of the invention is to provide a novel basic compound suited for use in the resist composition.

The inventor has found that basic compounds of general formula (1), especially general formulae (2) to (7) below which bear polar functional groups such as ester, cyano or acetal and have a benzimidazole skeleton can be prepared easily and in a high yield by the methods described later. When added in an appropriate amount to a resist, these compounds are highly effective for preventing a loss of resist film thickness and endow the resist composition with a high resolution and a focus margin widening effect.

The present invention provides resist compositions, patterning processes, and basic compounds, defined below.

[I] A resist composition comprising one or more basic compounds represented by the general formulae (1) to (7).

(1)

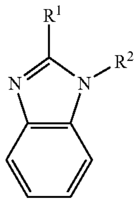

(2)

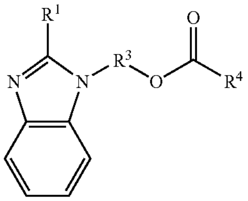

(3)

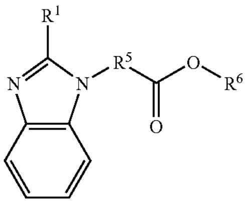

(4)

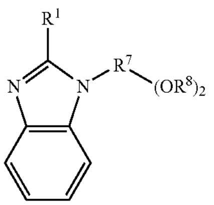

(5)

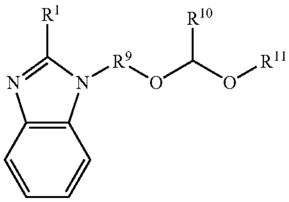

-continued (6)

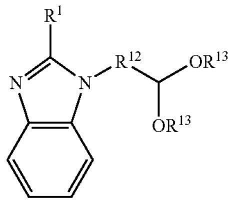

(7)

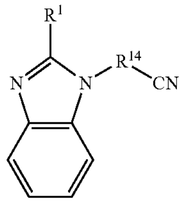

Herein $R^1$ is a hydrogen atom, a straight, branched or cyclic alkyl group of 1 to 10 carbon atoms, an aryl group of 6 to 10 carbon atoms, or an aralkyl group of 7 to 10 carbon atoms; $R^2$ is a polar functional group-bearing straight, branched or cyclic alkyl group of 1 to 20 carbon atoms wherein said alkyl group contains as the polar functional group at least one group selected from among ester, acetal and cyano groups, and optionally at least one group selected from among hydroxyl, carbonyl, ether, sulfide and carbonate groups; $R^3$, $R^5$, $R^9$, $R^{12}$ and $R^{14}$ are each independently a straight, branched or cyclic alkylene group of 1 to 10 carbon atoms; $R^4$ is a hydrogen atom or an alkyl group of 1 to 15 carbon atoms which may contain at least one group selected from among hydroxyl, carbonyl, ester, ether, sulfide, carbonate, cyano and acetal groups; $R^6$ is an alkyl group of 1 to 15 carbon atoms which may contain at least one group selected from among hydroxyl, carbonyl, ester, ether, sulfide, carbonate, cyano and acetal groups; $R^7$ is a trivalent, straight, branched or cyclic hydrocarbon group of 2 to 10 carbon atoms; $R^8$ is each independently an acyl group of 1 to 10 carbon atoms which may contain at least one ester or ether group, or two $R^8$ may bond together to form a cyclic carbonate or cyclic acetal; $R^{10}$ is a hydrogen atom or a straight, branched or cyclic alkyl group of 1 to 10 carbon atoms; $R^{11}$ is a straight, branched or cyclic alkyl group of 1 to 10 carbon atoms which may contain at least one group selected from among ether, sulfide and acetal groups, or $R^{10}$ and $R^{11}$ may bond together to form a ring; and $R^{13}$ is a straight, branched or cyclic alkyl group of 1 to 10 carbon atoms, or two $R^{13}$ may bond together to form a ring.

[II] A positive-working resist composition comprising:

(A) the basic compound of [I];

(B) an organic solvent;

(C) a base resin having an acid labile group-protected acidic functional group which is alkali-insoluble or substantially alkali-insoluble, but becomes alkali-soluble when the acid labile group is eliminated;

(D) a photoacid generator; and optionally, (E) a dissolution inhibitor.

[III] A negative-working resist composition comprising:

(A) the basic compound of [I];

(B) an organic solvent;

(C') a base resin which is alkali-soluble, but becomes substantially alkali-insoluble when crosslinked with a crosslinking agent;

(D) a photoacid generator; and (F) a crosslinking agent which induces crosslinkage under the action of an acid.

[IV] A patterning process comprising the steps of:

(1) applying the resist composition of [II] or [III] onto a substrate;

(2) heat treating the applied resist, then exposing the heat-treated resist through a photomask to high-energy radiation having a wavelength of at most 300 nm or an electron beam; and (3) heat treating the exposed resist, then developing the resist with a liquid developer.

[V] Basic compounds represented by the general formulae (2) to (6).

(2)

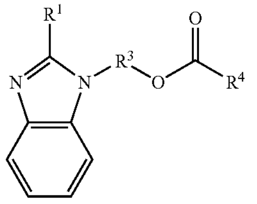

(3)

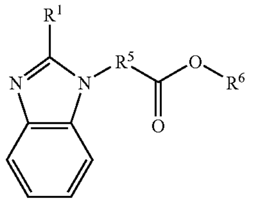

(4)

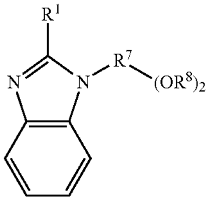

(5)

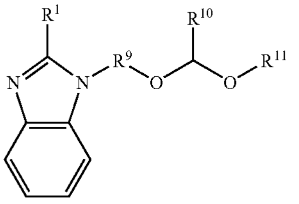

(6)

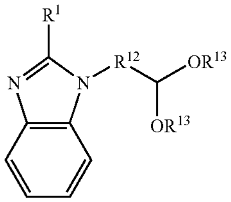

(7)

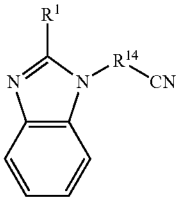

Herein $R^1$ is a hydrogen atom, a straight, branched or cyclic alkyl group of 1 to 10 carbon atoms, an aryl group of 6 to 10 carbon atoms, or an aralkyl group of 7 to 10 carbon atoms; $R^3$, $R^5$, $R^9$, $R^{12}$ and $R^{14}$ are each independently a straight, branched or cyclic alkylene group of 1 to 10 carbon atoms; $R^4$ is a hydrogen atom or an alkyl group of 1 to 15 carbon atoms which may contain at least one group selected from among hydroxyl, carbonyl, ester, ether, sulfide, carbonate, cyano and acetal groups; $R^6$ is an alkyl group of 1 to 15 carbon atoms which may contain at least one group selected from among hydroxyl, carbonyl, ester, ether, sulfide, carbonate, cyano and acetal groups; $R^6$ is a trivalent, straight, branched or cyclic hydrocarbon group of 2 to 10 carbon atoms; $R^8$ is each independently an acyl group of 1 to 10 carbon atoms which may contain at least one ester or ether group, or two $R^8$ may bond together to form a cyclic carbonate or cyclic acetal; $R^{10}$ is a hydrogen atom or a straight, branched or cyclic alkyl group of 1 to 10 carbon atoms; $R^{11}$ is a straight, branched or cyclic alkyl group of 1 to 10 carbon atoms which may contain at least one group selected from among ether, sulfide and acetal groups, or $R^{10}$ and $R^{11}$ may bond together to form a ring; and $R^{13}$ is a straight, branched or cyclic alkyl group of 1 to 10 carbon atoms, or two $R^{13}$ may bond together to form a ring.

DETAILED DESCRIPTION OF THE INVENTION

The resist composition of the invention comprises one or more basic compounds having a benzimidazole skeleton and a polar functional group, represented by the general formula (1).

(1)

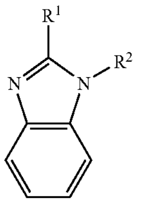

In formula (1), $R^1$ is a hydrogen atom, a straight, branched or cyclic alkyl group of 1 to 10 carbon atoms, an aryl group of 6 to 10 carbon atoms, or an aralkyl group of 7 to 10 carbon atoms. $R^2$ is a polar functional group-bearing, straight, branched or cyclic alkyl group of 1 to 20 carbon atoms, and the alkyl group contains as the polar functional group at least one group selected from among ester, acetal and cyano groups, and may additionally contain at least one group selected from among hydroxyl, carbonyl, ether, sulfide and carbonate groups.

Of the basic compounds of formula (1), basic compounds having a benzimidazole skeleton and a polar functional group, represented by the general formulae (2) to (7) below are preferred. The preferred resist composition comprises one or more basic compounds represented by formulae (2) to (7). It is noted that basic compounds of formulae (2) to (7) are novel.

(2)

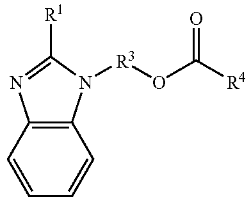

-continued (3)

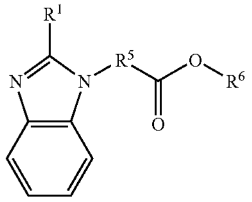

(4)

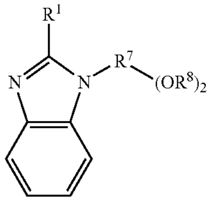

(5)

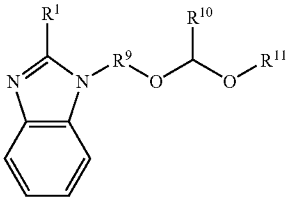

(6)

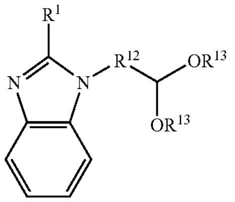

(7)

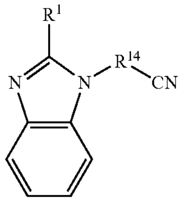

Herein $R^1$ is a hydrogen atom, a straight, branched or cyclic alkyl group of 1 to 10 carbon atoms, an aryl group of 6 to 10 carbon atoms, or an aralkyl group of 7 to 10 carbon atoms; $R^3$, $R^5$, $R^9$, $R^{12}$ and $R^{14}$ are each independently a straight, branched or cyclic alkylene group of 1 to 10 carbon atoms; $R^4$ is a hydrogen atom or an alkyl group of 1 to 15 carbon atoms which may contain at least one group selected from among hydroxyl, carbonyl, ester, ether, sulfide, carbonate, cyano and acetal groups; $R^6$ is an alkyl group of 1 to 15 carbon atoms which may contain at least one group selected from among hydroxyl, carbonyl, ester, ether, sulfide, carbonate, cyano and acetal groups; $R^7$ is a trivalent, straight, branched or cyclic hydrocarbon group of 2 to 10 carbon atoms; $R^8$ is each independently an acyl group of 1 to 10 carbon atoms which may contain at least one ester or ether group, or two $R^8$ may bond together to form a cyclic carbonate or cyclic acetal; $R^{10}$ is a hydrogen atom or a straight, branched or cyclic alkyl group of 1 to 10 carbon atoms; $R^{11}$ is a straight, branched or cyclic alkyl group of 1 to 10 carbon atoms which may contain at least one group selected from among ether, sulfide and acetal groups, or $R^{10}$ and $R^{11}$ may bond together to form a ring; $R^{13}$ is a straight, branched or cyclic alkyl group of 1 to 10 carbon atoms, or two $R^{13}$ may bond together to form a ring.

In formulae (1) to (7), $R^1$ is a hydrogen atom, a straight, branched or cyclic alkyl group of 1 to 10 carbon atoms, an aryl group of 6 to 10 carbon atoms, or an aralkyl group of 7 to 10 carbon atoms. Examples of suitable alkyl, aryl and aralkyl groups include, but are not limited to, methyl, ethyl, propyl, isopropyl, butyl, isobutyl, pentyl, hexyl, decyl, cyclopentyl, cyclohexyl, phenyl, tolyl, xylyl, naphthyl, benzyl and phenethyl.

In formula (1), $R^2$ is a polar functional group-bearing, straight, branched or cyclic alkyl group of 1 to 20 carbon atoms. The alkyl group contains as the polar functional group at least one group selected from among ester, acetal and cyano groups, and may additionally contain at least one group selected from among hydroxyl, carbonyl, ether, sulfide and carbonate groups. Illustrative, non-limiting examples include 2-oxotetrahydrofuran-3-yl, 5-oxotetrahydrofuran-3-yl, 2-oxotetrahydro-2H-pyran-3-yl, 3,3-dicyanopropyl, and 3,3-bis(methoxycarbonyl)propyl groups as well as groups having some of $R^3$, $R^4$, $R^5$, $R^6$, $R^7$, $R^8$, $R^9$, $R^{10}$, $R^{11}$, $R^{12}$, $R^{13}$ and $R^{14}$ such as $—R^3—OCO—R^4$, $—R^5—CO_2—R^6$, $—R^7—(OR^8)_2$, $—R^9—OCH(R^{10})—OR^{11}$, $—R^{12}—CH—(OR^{13})_2$ and $—R^{14}—CN$.

In formulae (2), (3), (5), (6) and (7), $R^3$, $R^5$, $R^9$, $R^{12}$ and $R^{14}$ represent straight, branched or cyclic alkylene groups of 1 to 10 carbon atoms, examples of which include, but are not limited to, methylene, ethylene, ethylidene, propylene, propylidene, isopropylidene, 1,3-propanediyl, 1,4-butanediyl, 1,2-butanediyl, 1,5-pentanediyl, 1,2-pentanediyl, 1,10-decanediyl, 1,2-cyclopentanediyl, 1,2-cyclohexanediyl, and 1,4-cyclohexanediyl.

In formulae (2) and (3), $R^4$ and $R^6$ represent straight, branched or cyclic alkyl groups of 1 to 15 carbon atoms which may contain at least one group selected from among hydroxyl, carbonyl, ester, ether, sulfide, carbonate, cyano and acetal groups. Specific, non-limiting examples of suitable alkyl groups include methyl, ethyl, propyl, isopropyl, butyl, isobutyl, pentyl, hexyl, decyl, pentadecyl, cyclopentyl, cyclohexyl, 2-tetrahydrofuryl, 2-oxo-3-tetrahydrofuryl, 2-tetrahydro-2H-pyranyl, tetrahydrofurfuryl, methoxymethyl, ethoxymethyl, propoxymethyl, (2-methoxyethoxy)methyl, cyanomethyl, methylthiomethyl, acetoxymethyl, formyloxymethyl, 1,3-dioxolan-4-ylmethyl, (2,2-dimethyl-1,3-dioxolan-4-yl)methyl, (2-oxo- 1,3-dioxolan-4-yl)methyl, methoxycarbonyl, ethoxycarbonyl, t-butoxycarbonyl, 2-hydroxyethyl, 1-methoxyethyl, 2-methoxyethyl, 1-ethoxyethyl, 2-ethoxyethyl, 2-propoxyethyl, 2-(2-methoxyethoxy)ethyl, 2-(2-tetrahydro-2H-pyranyloxy)ethyl, 2-formyloxyethyl, 2-acetoxyethyl, 2-propionyloxyethyl, 2-butyryloxyethyl, 2-valeryloxyethyl, 2-hexanoyloxyethyl, 2-cyanoethyl, 2-methylthioethyl, 2-methoxycarbonyloxyethyl, 2,2-dimethoxyethyl, 2,2-diethoxyethyl, 3,3-dimethoxypropyl, 3,3-diethoxypropyl, 2-hydroxypropyl, 2-methoxypropyl, 2-acetoxypropyl, 2-propionyloxypropyl, 3-hydroxypropyl, and 4-hydroxybutyl.

In formula (4), $R^7$ is a trivalent, straight, branched or cyclic hydrocarbon group of 2 to 10 carbon atoms, examples of which include 1,2,3-propanetriyl, 1,2,3-butanetriyl, 1,2,4-butanetriyl, 1,2,3-pentanetriyl, 2-methylpropane-1,1',3-triyl, 2,2-dimethylpropane-1,1',3-triyl, cyclohexane-1,2,3-triyl, and cyclohexane-1,3,5-triyl, but are not limited thereto.

In formula (4), $R^8$ which may be the same or different is an acyl group of 1 to 10 carbon atoms which may contain one or more ester or ether groups. Alternatively, two $R^8$ may bond together to form a cyclic carbonate or cyclic acetal.

Illustrative, non-limiting examples of the acyl groups represented by $R^8$ include formyl, acetyl, propionyl, butyryl, isobutyryl, valeryl, hexanoyl, octanoyl, decanoyl, pivaloyl, hexanecarbonyl, methoxyacetyl, (2-methoxyethoxy)acetyl, [2-(2-methoxyethoxy)ethoxy]acetyl, acetoxyacetyl, 2-tetrahydrofurancarbonyl, methoxycarbonyl, and t-butoxycarbonyl. In the event two $R^8$ bond together to form a cyclic carbonate or cyclic acetal, $R^8$ is a carbonyl group or an alkylidene group. Examples of alkylidene groups include, but are not limited to, methylene, ethylidene, propylidene and isopropylidene.

In formula (5), $R^{10}$ is a hydrogen atom or a straight, branched or cyclic alkyl group of 1 to 10 carbon atoms. Examples of such alkyl groups include, but are not limited to, methyl, ethyl, propyl, isopropyl, cyclohexyl, and decyl. $R^{11}$ is a straight, branched or cyclic alkyl group of 1 to 10 carbon atoms which may contain at least one group selected from among ether, sulfide and acetal groups. Examples include, but are not limited to, methyl, ethyl, propyl, isopropyl, butyl, isobutyl, pentyl, hexyl, decyl, cyclopentyl, cyclohexyl, methoxymethyl, 2-methoxyethyl, and methylthiomethyl. When $R^{10}$ and $R^{11}$ bond together to form a ring, examples of the ring include tetrahydrofuran and tetrahydro-2H-pyran, but are not limited thereto.

In formula (6), $R^{13}$ is a straight, branched or cyclic alkyl group of 1 to 10 carbon atoms, examples of which include methyl, ethyl, propyl, isopropyl, butyl, isobutyl, pentyl, hexyl and decyl. When two $R^{13}$ bond together to form a ring, examples of the ring include 1,3-dioxolane and 1,3-dioxane, but are not limited thereto.

Specific examples of the basic compounds having a benzimidazole skeleton and a polar functional group according to the invention include, but are not limited to, the following. In the structural formulas that appear below, "Me" represents methyl, "Et" represents ethyl, "t-Bu" represents t-butyl, "Ac" represents acetyl and "Ph" represents phenyl.

Amine 1

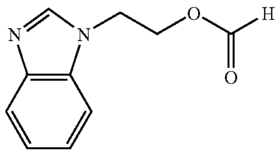

Amine 2

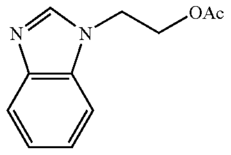

Amine 3

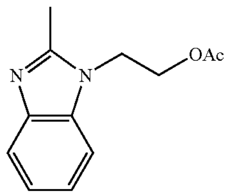

-continued

Amine 4

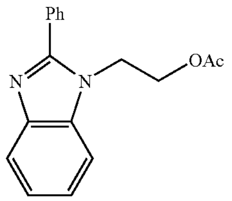

Amine 5

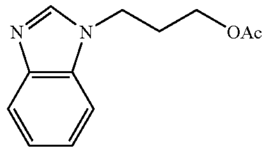

Amine 6

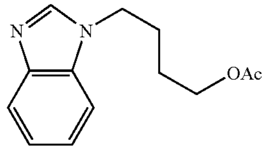

Amine 7

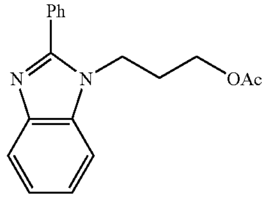

Amine 8

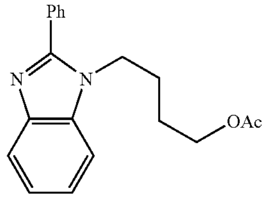

Amine 9

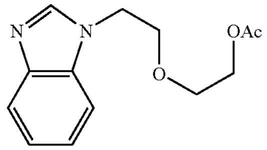

Amine 10

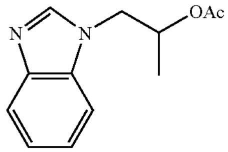

Amine 11

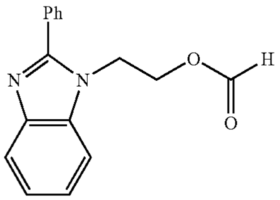

Amine 12

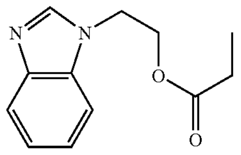

-continued
Amine 13
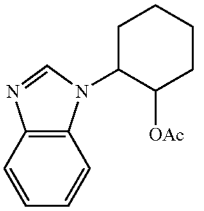
Amine 14
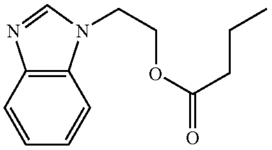
Amine 15
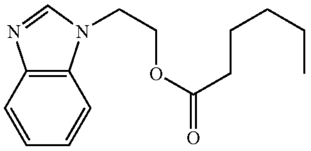
Amine 16
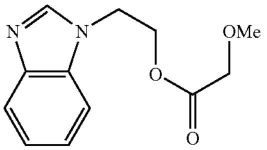
Amine 17
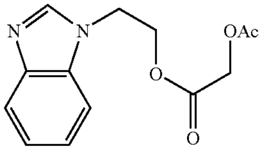
Amine 18
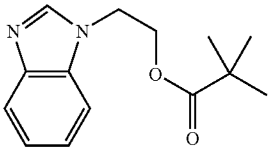
Amine 19
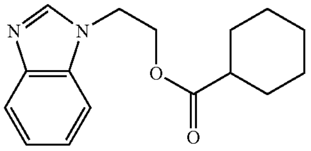
Amine 20
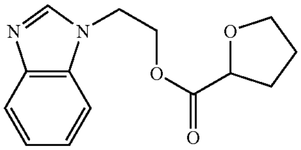
Amine 21
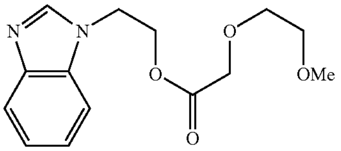
-continued
Amine 22
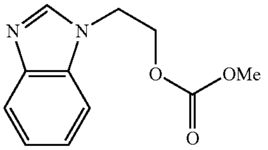
Amine 23
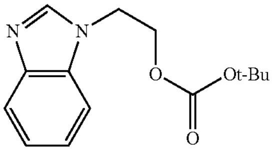
Amine 24
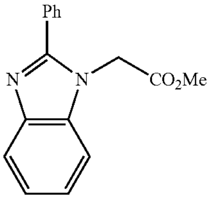
Amine 25
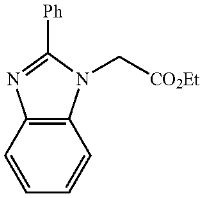
Amine 26
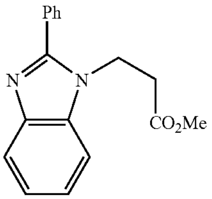
Amine 27
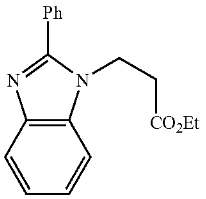
Amine 28
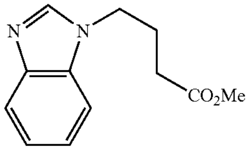
Amine 29
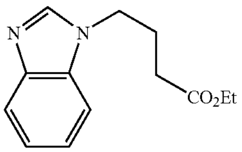

-continued
Amine 30
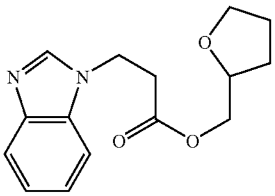
Amine 31
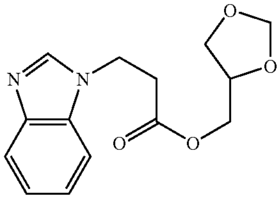
Amine 32
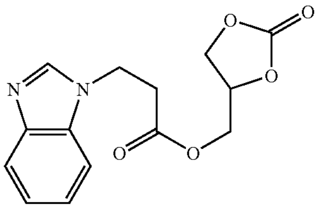
Amine 33
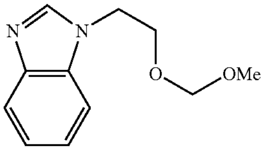
Amine 34
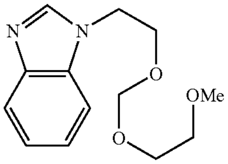
Amine 35
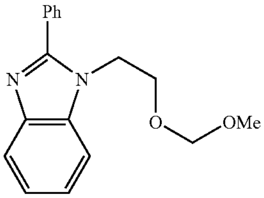
Amine 36
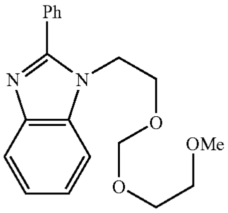
Amine 37
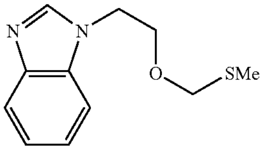
-continued
Amine 38
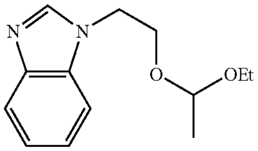
Amine 39
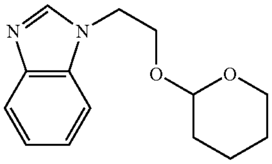
Amine 40
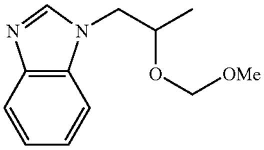
Amine 41
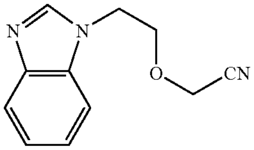
Amine 42
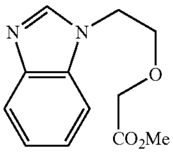
Amine 43
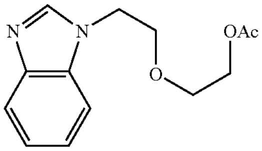
Amine 44
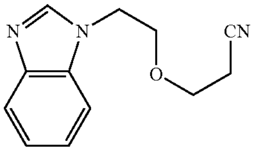
Amine 45
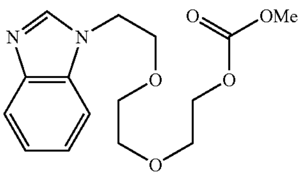
Amine 46
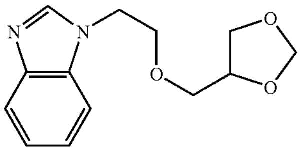

-continued
Amine 47
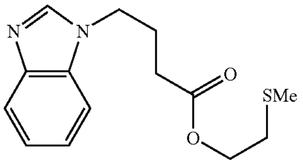
Amine 48
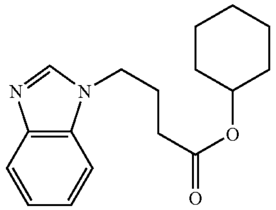
Amine 49
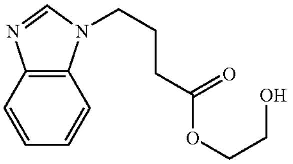
Amine 50
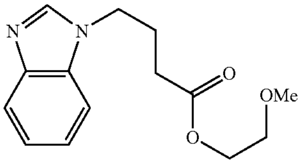
Amine 51
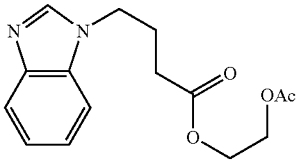
Amine 52
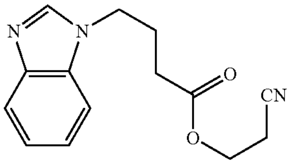
Amine 53
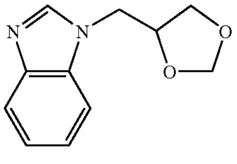
Amine 54
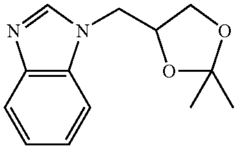
Amine 55
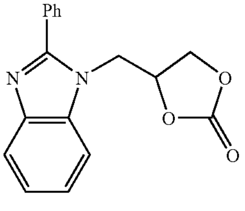
-continued
Amine 56
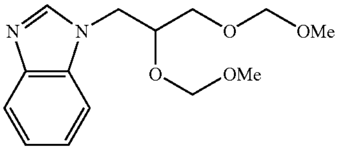
Amine 57
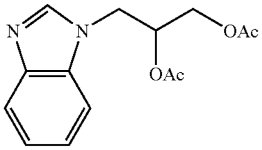
Amine 58
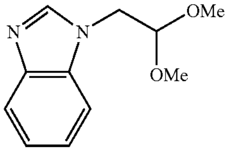
Amine 59
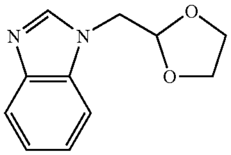
Amine 60
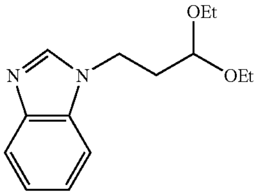
Amine 61
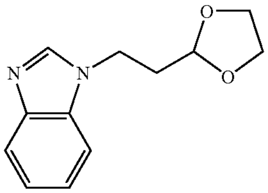
Amine 62
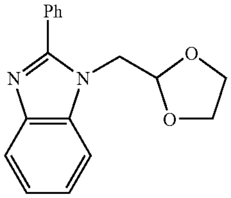
Amine 63
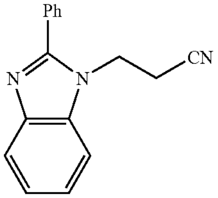
Amine 64
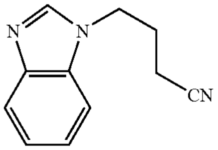

-continued

Amine 65

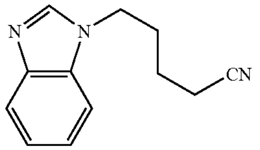

Amine 66

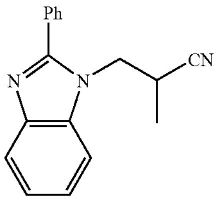

Amine 67

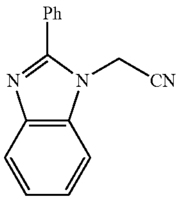

Amine 68

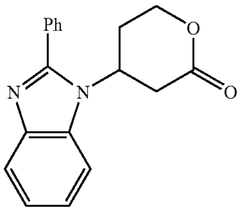

Amine 69

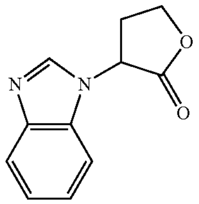

Amine 70

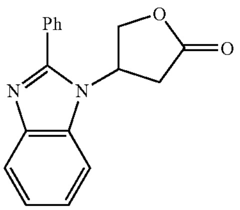

Amine 71

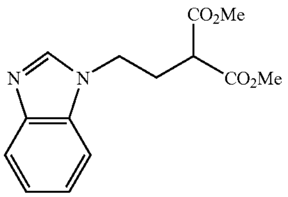

-continued

Amine 72

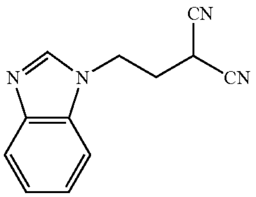

According to the invention, the basic compounds have a benzimidazole skeleton and a polar functional group moiety within the molecule. The polar functional group having a high kinetic affinity to acids (such as ester, acetal or cyano) can be placed at a suitable position near the amine nitrogen in benzimidazole that ultimately captures the acid. As a result, generated acids can be rapidly captured, enabling photoresists containing these basic compounds to achieve a high resolution and a wide focus margin. By selecting an optimal combination from among the possible combinations of $R^1$ and $R^2$ in formula (1), the basicity, acid capturing rate and diffusion rate within the resist can be suitably adjusted. Therefore, the basic compound additives are compatible with a broad range of resist polymers and photoacid generators.

The inventive resist composition is most preferably either a positive-working chemical amplification resist composition which includes:

(A) the above-described basic compound, (B) an organic solvent, (C) a base resin having an acid labile group-protected acidic functional group, which is alkali-insoluble or substantially alkali-insoluble, but becomes alkali-soluble when the acid labile group is eliminated, (D) a photoacid generator and optionally, (E) a dissolution inhibitor; or a negative-working chemical amplification resist composition which includes:

(A) the above-described basic compound, (B) an organic solvent, (C') a base resin which is alkali-soluble, but becomes substantially alkali-insoluble when crosslinked with a crosslinking agent (F), (D) a photoacid generator, and (F) a crosslinking agent which induces crosslinkage under the action of an acid.

These components are described in detail.

(B) Organic Solvent

The organic solvent used herein may be any organic solvent in which the base resin, photoacid generator, and other components are soluble. Illustrative, non-limiting, examples of the organic solvent include ketones such as cyclohexanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, propylene glycol monomethyl ether acetate, cyclohexanone and mixtures thereof because the photoacid generator is most soluble therein.

An appropriate amount of the organic solvent used is about 200 to 3,000 parts, especially about 400 to 2,000 parts by weight per 100 parts by weight of the base resin.

(C) Base Polymer

The base polymers used as component (C) or (C') in the inventive compositions include polyhydroxystyrene (PHS), and copolymers of PHS with styrene, (meth)acrylic acid esters or other polymerizable olefinic compounds, for KrF excimer laser resist use; (meth)acrylic acid ester polymers, alternating copolymers of cycloolefin with maleic anhydride, copolymers containing vinyl ethers or (meth)acrylic acid esters, polynorbornene, and ring-opening metathesis polymerized cycloolefins, for ArF excimer laser resist use; and fluorinated forms of the foregoing polymers (for both KrF and ArF laser uses) for $F_2$ excimer laser resist use, although the base polymers are not limited thereto. The base polymers may be used alone or in admixture of two or more. In the case of positive resist compositions, it is a common practice to substitute acid labile groups for hydroxyl groups on phenol, carboxyl groups or fluorinated alkyl alcohols for reducing the rate of dissolution in unexposed regions.

The acid labile groups to be introduced into the base polymers may be selected from a variety of such groups, preferably from acetal groups of 2 to 30 carbon atoms and tertiary alkyl groups of 4 to 30 carbon atoms having the formulae (C1) and (C2), respectively.

(C1)

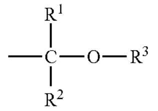

(C2)

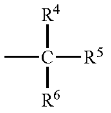

In formulae (C1) and (C2), $R^1$ and $R^2$ each are hydrogen or a straight, branched or cyclic $C_1$–$C_{20}$ alkyl group, which may contain a hetero atom such as oxygen, sulfur, nitrogen or fluorine, $R^3$, $R^4$, $R^5$ and $R^6$ each are a straight, branched or cyclic $C_1$–$C_{20}$ alkyl group, a $C_6$–$C_{10}$ aryl group or a $C_7$–$C_{10}$ aralkyl group, which may contain a hetero atom such as oxygen, sulfur, nitrogen or fluorine. A pair of $R^1$ and $R^2$, a pair of $R^1$ and $R^3$, a pair of $R^2$ and $R^3$, a pair of $R^4$ and $R^5$, a pair of $R^4$ and $R^6$, or a pair of $R^5$ and $R^6$, taken together, may form a ring with the carbon atom to which they are attached.

Illustrative examples of the acetal group of formula (C1) include, but are not limited to, methoxymethyl, ethoxymethyl, propoxymethyl, butoxymethyl, isopropoxymethyl, t-butoxymethyl, 1-methoxyethyl, 1-methoxypropyl, 1-methoxybutyl, 1-ethoxyethyl, 1-ethoxypropyl, 1-ethoxybutyl, 1-propoxyethyl, 1-propoxypropyl, 1-propoxybutyl, 1-cyclopentyloxyethyl, 1-cyclohexyloxyethyl, 2-methoxyisopropyl, 2-ethoxyisopropyl, 1-phenoxyethyl, 1-benzyloxyethyl, 1-phenoxypropyl, 1-benzyloxypropyl, 1-adamantyloxyethyl, 1-adamantyloxypropyl, 2-tetrahydrofuryl, 2-tetrahydro-2H-pyranyl, 1-(2-cyclohexanecarbonyloxyethoxy)ethyl, 1-(2-cyclohexanecarbonyloxyethoxy)propyl, 1-[2-(1-adamantylcarbonyloxy)ethoxy]ethyl, and 1-[2-(1-adamantylcarbonyloxy)ethoxy]propyl.

Illustrative examples of the tertiary alkyl group of formula (C2) include, but are not limited to, t-butyl, t-pentyl, 1-ethyl-1-methylpropyl, 1,1-diethylpropyl, 1,1,2-trimethylpropyl, 1-adamantyl-1-methylethyl, 1-methyl-1-(2-norbornyl)ethyl, 1-methyl-1-(tetrahydrofuran-2-yl)ethyl, 1-methyl-1-(7-oxanorbornan-2-yl)ethyl, 1-methylcyclopentyl, 1-ethylcyclopentyl, 1-propylcyclopentyl, 1-cyclopentylcyclopentyl, 1-cyclohexylcyclopentyl, 1-(2-tetrahydrofuryl)cyclopentyl, 1-(7-oxanorbornan-2-yl)cyclopentyl, 1-methylcyclohexyl, 1-ethylcyclohexyl, 1-cyclopentylcyclohexyl, 1-cyclohexylcyclohexyl, 2-methyl-2-norbornyl, 2-ethyl-2-norbornyl, 8-methyl-8-tricyclo[$5.2.1.0^{2,6}$]decyl, 8-ethyl-8-tricyclo[$5.2.1.0^{2,6}$]decyl, 3-methyl-3-tetracyclo[$4.4.0.1^{2,5}.1^{7,10}$]dodecyl, 3-ethyl-3-tetracyclo[$4.4.0.^{2,5}.1^{7,10}$]dodecyl, 2-methyl-2-adamantyl, 2-ethyl-2-adamantyl, 1-methyl-3-oxo-1-cyclohexyl, 1-methyl-1-(tetrahydrofuran-2-yl)ethyl, 5-hydroxy-2-methyl-2-adamantyl, and 5-hydroxy-2-ethyl-2-adamantyl.

In the base resin, at least 1 mol % of hydrogen atoms of hydroxyl groups may be substituted with acid labile groups of the following general formula (C3a) or (C3b) for crosslinkage between molecules or within a molecule.

(C3a)

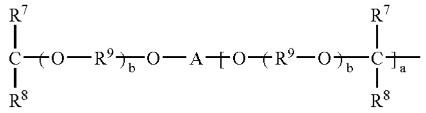

(C3b)

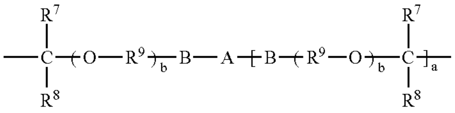

Herein, $R^7$ and $R^8$ each are hydrogen or a straight, branched or cyclic alkyl group of 1 to 8 carbon atoms, or $R^7$ and $R^8$, taken together, may form a ring, with the proviso that each of $R^7$ and $R^8$ is a straight or branched alkylene group of 1 to 8 carbon atoms when they form a ring. $R^9$ is a straight, branched or cyclic alkylene group of 1 to 10 carbon atoms. Letter "a" is an integer of 1 to 7 and "b" is 0 or an integer of 1 to 10. "A" is a (a+1)-valent aliphatic or alicyclic saturated hydrocarbon group, aromatic hydrocarbon group or heterocyclic group of 1 to 50 carbon atoms, which may have an intervening hetero atom and in which the hydrogen atom attached to a carbon atom may be partially replaced by a hydroxyl group, carboxyl group, carbonyl group or fluorine atom. B is —CO—O—, —NHCO—O— or —NHCONH—.

Illustrative examples of the crosslinking acetal linkages represented by formulae (C3a) and (C3b) are given below as (C3)-1 through (C3)-8, but not limited thereto.

(C3)-1

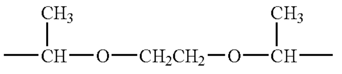

(C3)-2

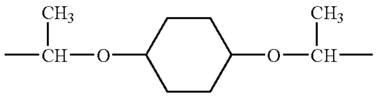

(C3)-3

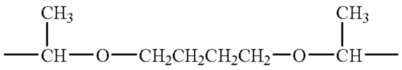

(C3)-4

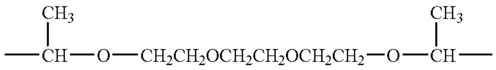

(C3)-5

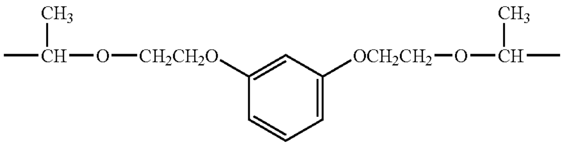

(C3)-6

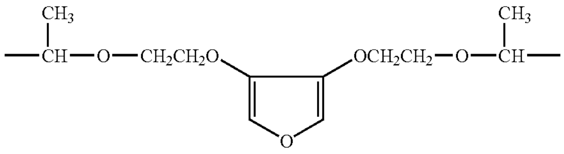

(C3)-7

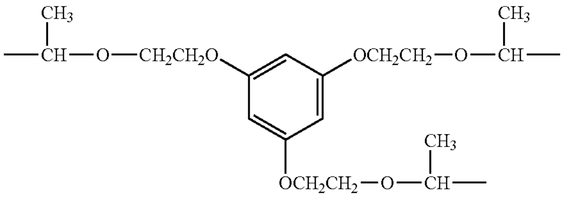

(C3)-8

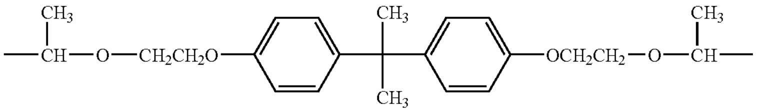

Preferably the base polymer has a weight average molecular weight of 2,000 to 100,000. With Mw below 2,000, film formation and resolution may become poor. With Mw beyond 100,000, resolution may become poor or foreign matter may generate during pattern formation.

(D) Photoacid Generator

The photoacid generator is a compound capable of generating an acid upon exposure to high energy radiation or electron beams and includes the following:

(i) onium salts of the formula (P1a-1), (P1a-2) or (P1b), (ii) diazomethane derivatives of the formula (P2), (iii) glyoxime derivatives of the formula (P3), (iv) bissulfone derivatives of the formula (P4), (v) sulfonic acid esters of N-hydroxyimide compounds of the formula (P5), (vi) β-ketosulfonic acid derivatives, (vii) disulfone derivatives, (viii) nitrobenzylsulfonate derivatives, (ix) sulfonate derivatives, and (x) oxime sulfonates.

These photoacid generators are described in detail.

(i) Onium Salts of Formula (P1a-1), (P1a-2) or (P1b):

(Pla-1)

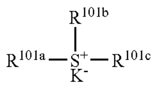

(Pla-2)

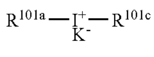

Herein, $R^{101a}$, $R^{101b}$, and $R^{101c}$ independently represent straight, branched or cyclic alkyl, alkenyl or oxoalkyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. $K^-$ is a non-nucleophilic counter ion.

$R^{101a}$, $R^{101b}$, and $R^{101c}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by $K^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

(P1b)

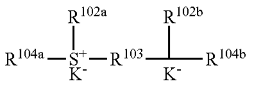

Herein, $R^{102a}$ and $R^{102b}$ independently represent straight, branched or cyclic alkyl groups of 1 to 8 carbon atoms. $R^{103}$ represents a straight, branched or cyclic alkylene groups of 1 to 10 carbon atoms. $R^{104a}$ and $R^{104b}$ independently represent 2-oxoalkyl groups of 3 to 7 carbon atoms. $K^-$ is a non-nucleophilic counter ion.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl. Illustrative examples of the counter ion represented by $K^-$ are the same as exemplified for formulae (P1a-1) and (P1a-2).

(ii) Diazomethane Derivatives of Formula (P2)

(P2)

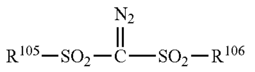

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime Derivatives of Formula (P3)

(P3)

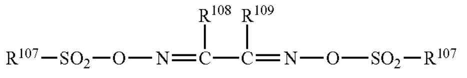

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone Derivatives of Formula (P4)

(P4)

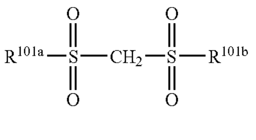

Herein, $R^{101a}$ and $R^{101b}$ are as defined above.

(v) Sulfonic Acid Esters of N-hydroxyimide Compounds of Formula (P5)

(P5)

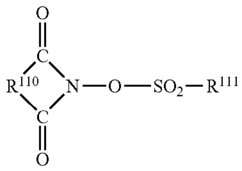

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, ethylene, trimethylene, tetramethylene, phenylethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; and the alkoxy groups of 1 to 4 carbon atoms include methoxy, ethoxy, propoxy, isopropoxy, n-butoxy, isobutoxy, and tert-butoxy. The phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl. The hetero-aromatic groups of 3 to 5 carbon atoms include pyridyl and furyl.

Illustrative examples of the photoacid generator include:

onium salts such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethane-sulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethane-sulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethane-sulfonate, (2-norbornyl)methyl(2-oxocyclohexyl)sulfonium trifluoro-methanesulfonate, ethylenebis[methyl(2-oxocyclopentyl)sulfonium trifluoro-methanesulfonate], and 1,2'-naphthylcarbonylmethyltetrahydrothiophenium triflate;

diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane;

glyoxime derivatives such as bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(p-toluenesulfonyl)-2-methyl-3,4-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(n-butanesulfonyl)-2,3-pentanedioneglyoxime, bis-O-(n-butanesulfonyl)-2-methyl-3,4-pentanedioneglyoxime, bis-O-(methanesulfonyl)-α-dimethylglyoxime, bis-O-(trifluoromethanesulfonyl)-α-dimethylglyoxime, bis-O-(1,1,1-trifluoroethanesulfonyl)-α-dimethylglyoxime, bis-O-(tert-butanesulfonyl)-α-dimethylglyoxime, bis-O-(perfluorooctanesulfonyl)-α-dimethylglyoxime, bis-O-(cyclohexanesulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-tert-butylbenzenesulfonyl)-α-dimethylglyoxime, bis-O-(xylenesulfonyl)-α-dimethylglyoxime, and bis-O-(camphorsulfonyl)-α-dimethylglyoxime;

bissulfone derivatives such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane;

β-ketosulfone derivatives such as 2-cyclohexylcarbonyl-2-(p-toluenesulfonyl)propane and 2-isopropylcarbonyl-2-(p-toluenesulfonyl)propane;

nitrobenzyl sulfonate derivatives such as 2,6-dinitrobenzyl p-toluenesulfonate and 2,4-dinitrobenzyl p-toluenesulfonate;

sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid esters of N-hydroxyimides such as N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethylbenzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethanesulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxyimide methanesulfonate, N-hydroxy-5-norbornene-2,3-dicarboxyimide trifluoromethanesulfonate, and N-hydroxy-5-norbornene-2,3-dicarboxyimide p-toluenesulfonate.

Preferred among these photoacid generators are onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethane-sulfonate, (2-norbornyl)methyl(2-oxocylohexyl)sulfonium trifluoro-methanesulfonate, and 1,2'-naphthylcarbonylmethyltetrahydrothiophenium triflate; diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; glyoxime derivatives such as bis-O-(p-toluenesulfonyl)-α-dimethylglyoxime and bis-O-(n-butanesulfonyl)-α-dimethylglyoxime; bissulfone derivatives such as bisnaphthylsulfonylmethane; and sulfonic acid esters of N-hydroxyimide compounds such as N-hydroxysuccinimide methanesulfonate, N-hydroxysuccinimide trifluoromethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide p-toluenesulfonate, N-hydroxynaphthalimide methanesulfonate, and N-hydroxynaphthalimide benzenesulfonate.

Also included are the oxime sulfonates described in U.S. Pat. No. 6,004,724, for example, (5-(4-toluenesulfonyl)oxyimino-5H-thiophen-2-ylidene)-phenylacetonitrile,
(5-(10-camphorsulfonyl)oxyimino-5H-thiophen-2-ylidene)-phenylacetonitrile,
(5-n-octanesulfonyloxyimino-5H-thiophen-2-ylidene)-phenylacetonitrile,
(5-(4-toluenesulfonyl)oxyimino-5H-thiophen-2-ylidene)(2-methylphenyl)acetonitrile,
(5-(10-camphorsulfonyl)oxyimino-5H-thiophen-2-ylidene)(2-methylphenyl)acetonitrile,
(5-n-octanesulfonyloxyimino-5H-thiophen-2-ylidene)(2-methylphenyl)acetonitrile, etc.

Also included are the oxime sulfonates described in U.S. Pat. No. 6,261,738 and JP-A 2000-314956, for example, 2,2,2-trifluoro-1-phenyl-ethanone oxime-O-methylsulfonate;
2,2,2-trifluoro-1-phenyl-ethanone oxime-O-(10-camphorylsulfonate);
2,2,2-trifluoro-1-phenyl-ethanone oxime-O-(4-methoxyphenyl-sulfonate);
2,2,2-trifluoro-1-phenyl-ethanone oxime-O-(1-naphthylsulfonate);
2,2,2-trifluoro-1-phenyl-ethanone oxime-O-(2-naphthylsulfonate);
2,2,2-trifluoro-1-phenyl-ethanone oxime-O-(2,4,6-trimethyl-phenylsulfonate);
2,2,2-trifluoro-1-(4-methylphenyl)-ethanone oxime-O-(10-camphorylsulfonate);
2,2,2-trifluoro-1-(4-methylphenyl)-ethanone oxime-O-(methylsulfonate);
2,2,2-trifluoro-1-(2-methylphenyl)-ethanone oxime-O-(10-camphorylsulfonate);
2,2,2-trifluoro-1-(2,4-dimethylphenyl)-ethanone oxime-O-(10-camphorylsulfonate);
2,2,2-trifluoro-1-(2,4-dimethylphenyl)-ethanone oxime-O-(1-naphthylsulfonate);
2,2,2-trifluoro-1-(2,4-dimethylphenyl)-ethanone oxime-O-(2-naphthylsulfonate);
2,2,2-trifluoro-1-(2,4,6-trimethylphenyl)-ethanone oxime-O-(10-camphorylsulfonate);
2,2,2-trifluoro-1-(2,4,6-trimethylphenyl)-ethanone oxime-O-(1-naphthylsulfonate);
2,2,2-trifluoro-1-(2,4,6-trimethylphenyl)-ethanone oxime-O-(2-naphthylsulfonate);
2,2,2-trifluoro-1-(4-methoxyphenyl)-ethanone oxime-O-methyl-sulfonate;
2,2,2-trifluoro-1-(4-methylthiophenyl)-ethanone oxime-O-methylsulfonate;
2,2,2-trifluoro-1-(3,4-dimethoxyphenyl)-ethanone oxime-O-methylsulfonate;
2,2,3,3,4,4,4-heptafluoro-1-phenyl-butanone oxime-O-(10-camphorylsulfonate);
2,2,2-trifluoro-1-(phenyl)-ethanone oxime-O-methylsulfonate;
2,2,2-trifluoro-1-(phenyl)-ethanone oxime-O-10-camphoryl-sulfonate;
2,2,2-trifluoro-1-(phenyl)-ethanone oxime-O-(4-methoxyphenyl)sulfonate;
2,2,2-trifluoro-1-(phenyl)-ethanone oxime-O-(1-naphthyl)-sulfonate;
2,2,2-trifluoro-1-(phenyl)-ethanone oxime-O-(2-naphthyl)-sulfonate;
2,2,2-trifluoro-1-(phenyl)-ethanone oxime-O-(2,4,6-trimethyl-phenyl)sulfonate;
2,2,2-trifluoro-1-(4-methylphenyl)-ethanone oxime-O-(10-camphoryl)sulfonate;
2,2,2-trifluoro-1-(4-methylphenyl)-ethanone oxime-O-methyl-sulfonate;
2,2,2-trifluoro-1-(2-methylphenyl)-ethanone oxime-O-(10-camphoryl)sulfonate;
2,2,2-trifluoro-1-(2,4-dimethylphenyl)-ethanone oxime-O-(1-naphthyl)sulfonate;
2,2,2-trifluoro-1-(2,4-dimethylphenyl)-ethanone oxime-O-(2-naphthyl)sulfonate;
2,2,2-trifluoro-1-(2,4,6-trimethylphenyl)-ethanone oxime-O-(10-camphoryl)sulfonate;
2,2,2-trifluoro-1-(2,4,6-trimethylphenyl)-ethanone oxime-O-(1-naphthyl)sulfonate;
2,2,2-trifluoro-1-(2,4,6-trimethylphenyl)-ethanone oxime-O-(2-naphthyl)sulfonate;
2,2,2-trifluoro-1-(4-methoxyphenyl)-ethanone oxime-O-methyl-sulfonate;
2,2,2-trifluoro-1-(4-thiomethylphenyl)-ethanone oxime-O-methylsulfonate;
2,2,2-trifluoro-1-(3,4-dimethoxyphenyl)-ethanone oxime-O-methylsulfonate;
2,2,2-trifluoro-1-(4-methoxyphenyl)-ethanone oxime-O-(4-methylphenyl)sulfonate;
2,2,2-trifluoro-1-(4-methoxyphenyl)-ethanone oxime-O-(4-methoxyphenyl)sulfonate;
2,2,2-trifluoro-1-(4-methoxyphenyl)-ethanone oxime-O-(4-dodecylphenyl)sulfonate;
2,2,2-trifluoro-1-(4-methoxyphenyl)-ethanone oxime-O-octylsulfonate;
2,2,2-trifluoro-1-(4-thiomethylphenyl)-ethanone oxime-O-(4-methoxyphenyl)sulfonate;
2,2,2-trifluoro-1-(4-thiomethylphenyl)-ethanone oxime-O-(4-dodecylphenyl)sulfonate;
2,2,2-trifluoro-1-(4-thiomethylphenyl)-ethanone oxime-O-octylsulfonate;
2,2,2-trifluoro-1-(4-thiomethylphenyl)-ethanone oxime-O-(2-naphthyl)sulfonate;
2,2,2-trifluoro-1-(2-methylphenyl)-ethanone oxime-O-methyl-sulfonate;
2,2,2-trifluoro-1-(4-methylphenyl)-ethanone oxime-O-phenylsulfonate;
2,2,2-trifluoro-1-(4-chlorophenyl)-ethanone oxime-O-phenylsulfonate;
2,2,3,3,4,4,4-heptafluoro-1-(phenyl)-butanone oxime-O-(10-camphoryl)sulfonate;
2,2,2-trifluoro-1-naphthyl-ethanone oxime-O-methylsulfonate;
2,2,2-trifluoro-2-naphthyl-ethanone oxime-O-methylsulfonate;
2,2,2-trifluoro-1-[4-benzylphenyl]-ethanone oxime-O-methyl-sulfonate;
2,2,2-trifluoro-1-[4-(phenyl-1,4-dioxa-but-1-yl)phenyl]-ethanone oxime-O-methylsulfonate;

2,2,2-trifluoro-1-naphthyl-ethanone oxime-O-propylsulfonate;

2,2,2-trifluoro-2-naphthyl-ethanone oxime-O-propylsulfonate;

2,2,2-trifluoro-1-[4-benzylphenyl]-ethanone oxime-O-propyl-sulfonate;

2,2,2-trifluoro-1-[4-methylsulfonylphenyl]-ethanone oxime-O-propylsulfonate; 1,3-bis[1-(4-phenoxyphenyl)-2,2,2-trifluoroethanone oxime-O-sulfonyl]phenyl;

2,2,2-trifluoro-1-[4-methylsulfonyloxyphenyl]-ethanone oxime-O-propylsulfonate;

2,2,2-trifluoro-1-[4-methylcarbonyloxyphenyl]-ethanone oxime-O-propylsulfonate;

2,2,2-trifluoro-1-[6H,7H-5,8-dioxonaphth-2-yl]-ethanone oxime-O-propylsulfonate;

2,2,2-trifluoro-1-[4-methoxycarbonylmethoxyphenyl]-ethanone oxime-O-propylsulfonate;

2,2,2-trifluoro-1-[4-(methoxycarbonyl)-(4-amino-1-oxa-pent-1-yl)-phenyl]-ethanone oxime-O-propylsulfonate;

2,2,2-trifluoro-1-[3,5-dimethyl-4-ethoxyphenyl]-ethanone oxime-O-propylsulfonate;

2,2,2-trifluoro-1-[4-benzyloxyphenyl]-ethanone oxime-O-propylsulfonate;

2,2,2-trifluoro-1-[2-thiophenyl]-ethanone oxime-O-propylsulfonate; and 2,2,2-trifluoro-1-[1-dioxa-thiophen-2-yl)]-ethanone oxime-O-propylsulfonate.

Also included are the oxime sulfonates described in JP-A 9-95479 and JP-A 9-230588 and the references cited therein, for example, α-(p-toluenesulfonyloxyimino)-phenylacetonitrile, α-(p-chlorobenzenesulfonyloxyimino)-phenylacetonitrile, α-(4-nitrobenzenesulfonyloxyimino)-phenylacetonitrile, α-(4-nitro-2-trifluoromethylbenzenesulfonyloxyimino)-phenylacetonitrile, α-(benzenesulfonyloxyimino)-4-chlorophenylacetonitrile, α-(benzenesulfonyloxyimino)-2,4-dichlorophenylacetonitrile, α-(benzenesulfonyloxyimino)-2,6-dichlorophenylacetonitrile, α-(benzenesulfonyloxyimino)-4-methoxyphenylacetonitrile, α-(2-chlorobenzenesulfonyloxyimino)-4-methoxyphenylaceto-nitrile, α-(benzenesulfonyloxyimino)-2-thienylacetonitrile, α-(4-dodecylbenzenesulfonyloxyimino)-phenylacetonitrile, α-[(4-toluenesulfonyloxyimino)-4-methoxyphenyl]acetonitrile, α-[(dodecylbenzenesulfonyloxyimino)-4-methoxyphenyl]aceto-nitrile, α-(tosyloxyimino)-3-thienylacetonitrile, α-(methylsulfonyloxyimino)-1-cyclopentenylacetonitrile, α-(ethylsulfonyloxyimino)-1-cyclopentenylacetonitrile, α-(isopropylsulfonyloxyimino)-1-cyclopentenylacetonitrile, α-(n-butylsulfonyloxyimino)-1-cyclopentenylacetonitrile, α-(ethylsulfonyloxyimino)-1-cyclohexenylacetonitrile, α-(isopropylsulfonyloxyimino)-1-cyclohexenylacetonitrile, and α-(n-butylsulfonyloxyimino)-1-cyclohexenylacetonitrile.

Suitable bisoxime sulfonates include those described in JP-A 9-208554, for example, bis(α-(4-toluenesulfonyloxy)imino)-p-phenylenediacetonitrile, bis(α-(benzenesulfonyloxy)imino)-p-phenylenediacetonitrile, bis(α-(methanesulfonyloxy)imino)-p-phenylenediacetonitrile, bis(α-(butanesulfonyloxy)imino)-p-phenylenediacetonitrile, bis(α-(10-camphorsulfonyloxy)imino)-p-phenylenediacetonitrile, bis(α-(4-toluenesulfonyloxy)imino)-p-phenylenediacetonitrile, bis(α-(trifluoromethanesulfonyloxy)imino)-p-phenylenediaceto-nitrile, bis(α-(4-methoxybenzenesulfonyloxy)imino)-p-phenylenediaceto-nitrile, bis(α-(4-toluenesulfonyloxy)imino)-m-phenylenediacetonitrile, bis(α-(benzenesulfonyloxy)imino)-m-phenylenediacetonitrile, bis(α-(methanesulfonyloxy)imino)-m-phenylenediacetonitrile, bis(α-(butanesulfonyloxy)imino)-m-phenylenediacetonitrile, bis(α-(10-camphorsulfonyloxy)imino)-m-phenylenediacetonitrile, bis(α-(4-toluenesulfonyloxy)imino)-m-phenylenediacetonitrile, bis(α-(trifluoromethanesulfonyloxy)imino)-m-phenylenediaceto-nitrile, bis(α-(4-methoxybenzenesulfonyloxy)imino)-m-phenylenediaceto-nitrile, etc.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.1 to 50 parts, and especially 0.5 to 40 parts by weight, per 100 parts by weight of the base resin. Less than 0.1 part of the photoacid generator may generate a less amount of acid upon exposure, sometimes leading to a poor sensitivity and resolution whereas more than 50 parts of the photoacid generator may adversely affect the transmittance and resolution of resist.

(E) Dissolution Inhibitor

To the resist composition, a dissolution inhibitor may be added. The dissolution inhibitor is a compound having on the molecule at least two phenolic hydroxyl groups, in which an average of from 0 to 100 molt of all the hydrogen atoms on the phenolic hydroxyl groups are replaced with acid labile groups or a compound having on the molecule at least one carboxyl group, in which an average of 50 to 100 molt of all the hydrogen atoms on the carboxyl groups are replaced with acid labile groups, both the compounds having an average molecular weight within a range of 100 to 1,000, and preferably 150 to 800.

The degree of substitution of the hydrogen atoms on the phenolic hydroxyl groups with acid labile groups is on average at least 0 mol %, and preferably at least 30 mol %, of all the phenolic hydroxyl groups. The upper limit is 100 mol %, and preferably 80 mol %. The degree of substitution of the hydrogen atoms on the carboxyl groups with acid labile groups is on average at least 50 mol %, and preferably at least 70 mol %, of all the carboxyl groups, with the upper limit being 100 mol %.

Preferable examples of such compounds having two or more phenolic hydroxyl groups or compounds having at least one carboxyl group include those of formulas (D1) to (D14) below.

(D1)

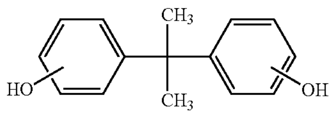

(D2)

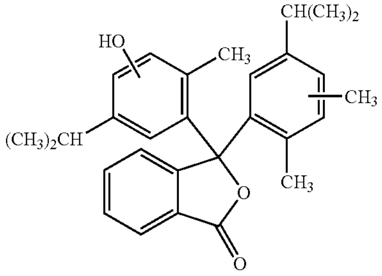

(D3)

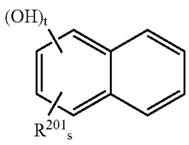

(D4)

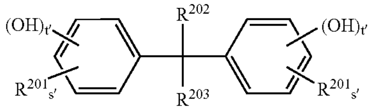

(D5)

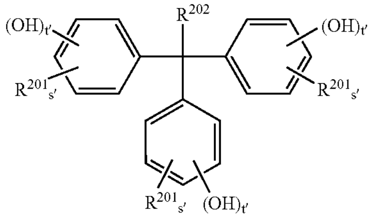

(D6)

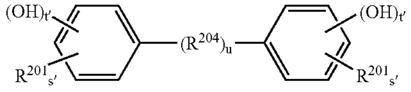

(D7)

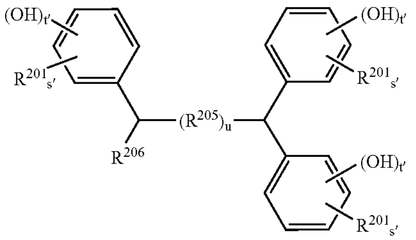

(D8)

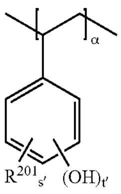

-continued (D9)

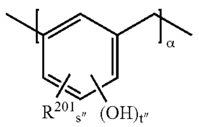

(D10)

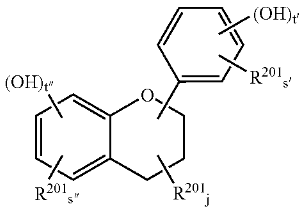

(D11)

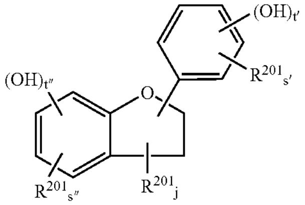

(D12)

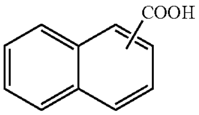

(D13)

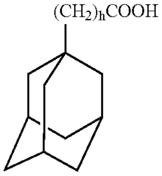

(D14)

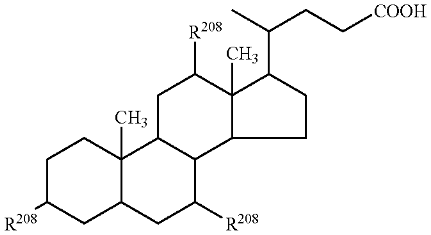

In these formulas, $R^{201}$, and $R^{202}$ are each hydrogen or a straight or branched alkyl or alkenyl of 1 to 8 carbon atoms; $R^{203}$ is hydrogen, a straight or branched alkyl or alkenyl of 1 to 8 carbon atoms, or $-(R^{207})_h-COOH$; $R^{204}$ is $-(CH_2)_i-$ (where i=2 to 10), an arylene of 6 to 10 carbon atoms, carbonyl, sulfonyl, an oxygen atom, or a sulfur atom; $R^{205}$ is an alkylene of 1 to 10 carbon atoms, an arylene of 6 to 10 carbon atoms, carbonyl, sulfonyl, an oxygen atom, or a sulfur atom; $R^{206}$ is hydrogen, a straight or branched alkyl or alkenyl of 1 to 8 carbon atoms, or a hydroxyl-substituted phenyl or naphthyl; $R^{207}$ is a straight or branched alkylene of 1 to 10 carbon atoms; $R^{208}$ is hydrogen or hydroxyl; the letter j is an integer from 0 to 5; u and h are each 0 or 1; s, t, s', t', s", and t" are each numbers which satisfy s+t=8, s'+t'=5, and s"+t"=4, and are such that each phenyl skeleton has at least one hydroxyl group; and a is a number such that the compounds of formula (D8) or (D9) have a molecular weight of from 100 to 1,000.

The above compounds have a weight average molecular weight within a range of 100 to 1,000, and preferably 150 to 800.

The dissolution inhibitor may be formulated in an amount of 0 to 50 parts, preferably 5 to 50 parts, and more preferably 10 to 30 parts by weight, per 100 parts by weight of the base resin, and may be used singly or as a mixture of two or more thereof. Too less an amount of the dissolution inhibitor may fail to improve resolution whereas the use of more than 50 parts may lead to slimming of the patterned film, and thus a decline in resolution.

(F) Crosslinker

Formulated in the negative resist composition is a crosslinker (F) which forms a crosslinked structure under the action of acid. Typical crosslinkers are compounds having at least two hydroxymethyl, alkoxymethyl, epoxy or vinyl ether groups within a molecule. Substituted glycoluril derivatives, urea derivatives, and hexa(methoxymethyl) melamine compounds are suitable as the crosslinker. Examples include N,N,N',N'-tetramethoxymethylurea, hexamethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred crosslinkers are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine.

In the resist composition, an appropriate amount of the crosslinker is, though not limited thereto, about 1 to 25 parts, and especially about 5 to 20 parts by weight per 100 parts by weight of the base resin in the composition. The crosslinkers may be used alone or in admixture of two or more.

In addition to the inventive basic compound, one or more of commonly used basic compounds may be employed in the inventive resist composition. Examples of suitable conventional basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropylamine, n-butylamine, iso-butylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, di-iso-propylamine, di-n-butylamine, di-iso-butylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, tri-iso-propylamine, tri-n-butylamine, tri-iso-butylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl) pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g. nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formula (B)-1 may also be included alone or in admixture.

$$N(X)_n(Y)_{3-n} \quad \text{(B)-1}$$

In the formula, n is equal to 1, 2 or 3; side chain Y is independently hydrogen or a straight, branched or cyclic alkyl group of 1 to 20 carbon atoms which may contain an ether or hydroxyl group; and side chain X is independently selected from groups of the following general formulas (X)-1 to (X)-3, and two or three X's may bond together to form a ring.

(X)-1

$$-[R^{300}-O-R^{301}]$$

(X)-2

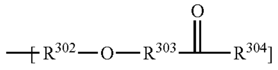

(X)-3

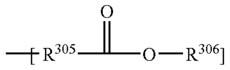

In the formulas, $R^{300}$, $R^{302}$ and $R^{305}$ are independently straight or branched alkylene groups of 1 to 4 carbon atoms; $R^{301}$ and $R^{304}$ are independently hydrogen, straight, branched or cyclic alkyl groups of 1 to 20 carbon atoms, which may contain at least one hydroxyl, ether, ester group or lactone ring; $R^{303}$ is a single bond or a straight or branched alkylene group of 1 to 4 carbon atoms; and $R^{306}$ is a straight, branched or cyclic alkyl group of 1 to 20 carbon atoms, which may contain at least one hydroxyl, ether, ester group or lactone ring.

Illustrative examples of the basic compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4,1-aza-15-crown-5,1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)ethyl-amine, N,N-bis(2-formyloxyethyl)-2-(2-formyloxyethoxycarbonyl)ethyl-amine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Also useful are one or more of cyclic structure-bearing basic compounds having the following general formula (B)-2.

(B)-2

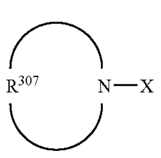

Herein X is as defined above, and $R^{307}$ is a straight or branched alkylene group of 2 to 20 carbon atoms which may contain one or more carbonyl, ether, ester or sulfide groups.

Illustrative examples of the cyclic structure-bearing basic compounds having formula (B)-2 include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]

ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

Also, one or more of cyano-bearing basic compounds having the following general formulae (B)-3 to (B)-6 may be blended.

(B)-3

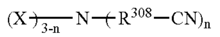

(B)-4

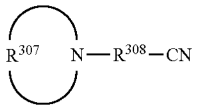

(B)-5

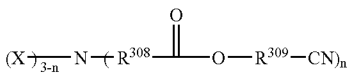

(B)-6

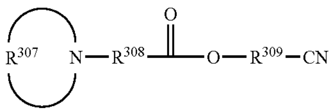

Herein, X, $R^{307}$ and n are as defined above, and $R^{308}$ and $R^{309}$ are each independently a straight or branched alkylene group of 1 to 4 carbon atoms.

Illustrative examples of the cyano-bearing basic compounds having formulae (B)-3 to (B)-6 include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiono-nitrile, N-(2-cyanoethyl)-N-(3-hydroxy-1-propyl)-3-aminopropiono-nitrile, N-(3-acetoxy-1-propyl)-N-(2-cyanoethyl)-3-aminopropiono-nitrile, N-(2-cyanoethyl)-N-(3-formyloxy-1-propyl)-3-aminopropiono-nitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl)aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-amino-propionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-amino-propionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

The conventional basic compounds may be used alone or in admixture of two or more. The conventional basic compound is preferably formulated in an amount of 0 to 2 parts, and especially 0 to 1 part by weight, per 100 parts by weight of the base resin.

In addition to the above components, the inventive resist composition may optionally include additives such as surfactants and acidic compounds.

Patterning with the inventive resist composition may be carried out by a conventional process. Such a process typically includes the steps of:

(1) applying the above-described chemical amplification resist composition onto a substrate;

(2) heat treating the applied resist, then exposing the heat-treated resist through a photomask to high-energy radiation having a wavelength of at most 300 nm, preferably at most 250 nm, or an electron beam; and (3) heat treating the exposed resist, then developing the resist with a liquid developer.

It is desirable for the basic compound of the invention to be included in an amount of 0.001 to 2 parts by weight, and especially 0.01 to 1 part by weight, per 100 parts by weight of the overall base resin. The use of less than 0.001 part may have no perceivable effect, whereas the use of more than 2 parts may lower the sensitivity of the resist.

Preferably, the basic compound of the invention having a benzimidazole skeleton and a polar functional group, represented by formulae (1) to (7), is prepared by a method which is selected optimal for the structure of the compound. Specific, non-limiting, examples are a method using N-alkylation reaction of benzimidazole compounds, and a method using O-acylation or O-alkylation reaction of benzimidazole compounds having a hydroxyalkyl substituent group on N. The preparation methods are described in detail.

The first method is a preparation method using N-alkylation reaction of benzimidazole compounds. Basically, the method is applicable to the synthesis of all basic compounds having formulae (1) to (7).

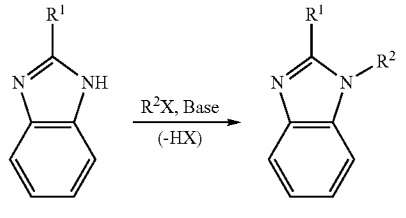

(8) (1)

In the above formulae, $R^1$ is a hydrogen atom, a straight, branched or cyclic alkyl group of 1 to 10 carbon atoms, an aryl group of 6 to 10 carbon atoms, or an aralkyl group of 7 to 10 carbon atoms. $R^2$ is a straight, branched or cyclic alkyl group of 1 to 20 carbon atoms which contains as a polar functional group at least one group selected from among ester, acetal and cyano groups, and optionally at least one group selected from among hydroxyl, carbonyl, ether, sulfide and carbonate groups. X is an eliminatable group such as a halogen atom, p-toluenesulfonyloxy, methanesulfonyloxy, trifluoromethanesulfonoxy or hydroxyl group.

In the above reaction, it is desirable to use the alkylating agent $R^2X$ in an amount of 0.3 to 10 moles, and especially 0.5 to 2 moles, per mole of the benzimidazole compound (8). The reaction may be carried out in a solvent or in the absence of a solvent. Solvents that may be selected in accordance with the reaction conditions and used, either singly or as mixtures thereof, include alcohols such as methanol, ethanol, isopropyl alcohol, t-butyl alcohol and ethylene glycol; hydrocarbons such as hexane, heptane, benzene, toluene and xylene; ethers such as diethyl ether, dibutyl ether, tetrahydrofuran, 1,4-dioxane and diglyme; chlorinated solvents such as methylene chloride, chloroform and 1,2-dichloroethylene; aprotic polar solvents such as N,N-dimethylformamide, N,N-dimethylacetamide, dimethylsulfoxide and N-methylpyrrolidone; carboxylic acids such as formic acid and acetic acid; esters such as ethyl acetate and butyl acetate; ketones such as acetone and 2-butanone; nitriles such as acetonitrile; amines such as pyridine and triethylamine; and water. The reaction temperature may be selected from a range of 0° C. to the reflux temperature of the solvent, in accordance with the reaction rate. The base used in the invention may be selected in accordance with the reaction conditions from among amines such as pyridine, triethylamine, diisopropylethylamine, 4-dimethylaminopyridine and imidazole; metal alkoxides such as sodium methoxide, sodium ethoxide and potassium t-butoxide; carbonates such as sodium carbonate, potassium carbonate and cesium carbonate; hydroxides such as sodium hydroxide, potassium hydroxide and tetramethylammonium hydroxide; metal hydrides such as sodium hydride and potassium hydride; organometallic compounds such as butyllithium and ethyl magnesium bromide; and metal amides such as lithium diisopropylamide. Any one or mixture of these bases may be used. It is desirable to use the base in an amount of from 0.3 to 10 moles, and especially from 1 to 5 moles per mole of the benzimidazole compound (8). An iodide such as sodium iodide, lithium iodide or tetrabutylammonium iodide, or a bromide such as sodium bromide, lithium bromide or tetrabutylammonium bromide, may be added as a catalyst to increase the reaction rate. When a catalyst is added, it is desirable for the amount of such addition to be from 0.001 to 2 moles, and especially from 0.005 to 0.5 mole, per mole of the benzimidazole compound (8). To maximize the final yield, it is desirable to monitor the progress of the reaction using gas chromatography (GC) or thin-layer chromatography (TLC) until the reaction is complete. Generally, the reaction time is about 0.5 to 100 hours. The target benzimidazole compound (1) having a polar functional group is obtained by a conventional aqueous work-up from the reaction mixture. If necessary, compound (1) can be purified by an ordinary method such as distillation, chromatography or recrystallization. Alternatively, it may be possible to omit the aqueous work-up, either by using filtration to collect the salt that has formed in the reaction and subjecting the collected salt to purification, or by furnishing the reaction mixture directly to purification.

Alternatively, the target benzimidazole compounds (1) having polar functional groups can be obtained, depending on the particular structure of the target compounds, by addition of benzimidazole compounds to α,β-unsaturated carbonyl compounds such as acrylic acid esters and acrylonitrile.

The second method is a preparation method using O-acylation or O-alkylation reaction of benzimidazole compounds having a hydroxyalkyl substituent group on N. This method is effective especially for the preparation of basic compounds having formulae (2), (4) and (5).

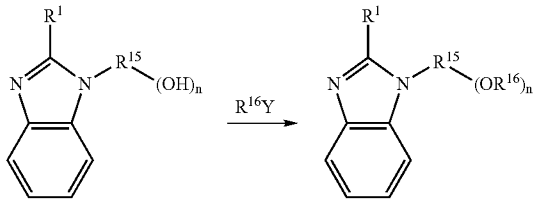

(9) (10)

In the formulae, $R^1$ is a hydrogen atom, a straight, branched or cyclic alkyl group of 1 to 10 carbon atoms, an aryl group of 6 to 10 carbon atoms, or an aralkyl group of 7 to 10 carbon atoms; $R^{15}$ is a (n+1)-valent, straight, branched or cyclic hydrocarbon group of 1 to 10 carbon atoms; $R^{16}$ is an acyl or 1-alkoxyalkyl group; Y is an eliminatable group such as a halogen atom, alkylsulfonyloxy, arylsulfonyloxy, hydroxyl, acyloxy, phenoxy, or alkoxy group, and n is equal to 1 or 2.

It is noted that the compounds (10) wherein n=1 and $R^{16}$=acyl correspond to compounds of formula (2), the compounds (10) wherein n=1 and $R^{16}$=1-alkoxyalkyl correspond to compounds of formula (5), and the compounds (10) wherein n=2 correspond to compounds of formula (4).

In the above reaction, the alkylating or acylating agent $R^{16}Y$ acts on the N-(hydroxyalkyl)benzimidazole compound (9), which has been prepared by the first method or by addition of benzimidazole compounds to cyclic ethers (e.g., ethylene oxide, propylene oxide, glycidol, oxetane) or carbonates (e.g., ethylene carbonate, propylene carbonate), yielding the target polar functional group-bearing benzimidazole compound (10).

When $R^{16}$ is an acyl group, examples of $R^{16}Y$ include, but are not limited to, formic acid, acetic formic anhydride, acetic anhydride, acetic chloride, propionic anhydride, propionic chloride, butyric chloride, isobutyric chloride, valeric chloride, pivalic chloride, methoxyacetic chloride, acetoxyacetic chloride, di-t-butyl pyrocarboxylate, phenyl acetate, p-nitrophenyl acetate, and 2,4,6-trichlorophenyl acetate. When $R^{16}$ is 1-alkoxyalkyl, examples of $R^{16}Y$ include, but are not limited to, methoxymethyl chloride, (2-methoxyethoxy)methyl chloride, (2-methylthioethoxy)methyl chloride, 1-chloro-1-ethoxyethane, 1-chloro-1-ethoxypropane, 1-chloro-1-propoxyethane, 2-chlorotetrahydrofuran, and 2-chloro-2H-tetrahydropyran. An appropriate amount of $R^{16}Y$ used per mole of the N-(hydroxyalkyl)benzimidazole compound (9) is from 0.5 to 5.0 moles, especially from 1.0 to 2.5 moles in the event n=1, and from 1.0 to 10 moles, especially from 2.0 to 5.0 moles in the event n=2.

The reaction may be carried out in a solvent or in the absence of a solvent. Solvents that may be selected in accordance with the reaction conditions and used, either singly or as mixtures thereof, include hydrocarbons such as hexane, heptane, benzene, toluene and xylene; ethers such as diethyl ether, dibutyl ether, tetrahydrofuran, 1,4-dioxane and diglyme; chlorinated solvents such as methylene chloride, chloroform and 1,2-dichloroethylene; aprotic polar solvents such as N,N-dimethylformamide, N,N-dimethylacetamide, dimethylsulfoxide and N-methylpyrrolidone; carboxylic acids such as formic acid and acetic acid; esters such as ethyl acetate and butyl acetate; ketones such as acetone and 2-butanone; nitriles such as acetonitrile; amines such as pyridine and triethylamine; alcohols such as methanol, ethanol, 2-propanol and t-butyl alcohol; and water.

In order to promote the reaction, a basic compound may be added. Examples include, but are not limited to, salts of alkali or alkaline earth metals such as sodium hydroxide, potassium hydroxide, potassium carbonate, sodium carbonate, sodium hydrogen carbonate, sodium hydride, calcium hydride, potassium t-butoxide, and lithium t-butoxide; organometal compounds such as n-butyllithium, lithium diisopropylamide, lithium hexamethyldisilazide, bromomagnesium diisopropylamide; and organic amines such as pyridine, triethylamine, diisopropylethylamine, N,N-dimethylaniline, and 4-dimethylaminopyridine. The basic compound may be used alone or in admixture. An appropriate amount of the basic compound used is from 0.8 to 10 moles, especially from 0.9 to 3.0 moles per mole of $R^{16}Y$. The reaction temperature may be selected from a range of −70° C. to the reflux temperature of the solvent, preferably 0° C. to 50° C. In the event $R^{16}$=acyl and Y=alkoxy, $R^{16}Y$ is a carboxylic acid ester, and the instant reaction is a transesterification reaction. In this event, the above-mentioned basic compound is used as a catalyst in an amount of 0.001 to 5.0 moles, especially 0.005 to 0.5 mole per mole of $R^{16}Y$, and reaction is preferably carried out while distilling off the alcohol (Y—H) formed during the reaction. To maximize the final yield, it is desirable to monitor the progress of the reaction using gas chromatography (GC) or thin-layer chromatography (TLC) until the reaction is complete. Generally, the reaction time is about 0.2 to 20 hours. The target polar functional group-bearing benzimidazole compound (10) is obtained by a conventional aqueous work-up from the reaction mixture. If necessary, compound (10) can be purified by an ordinary method such as distillation, chromatography or recrystallization. Alternatively, it may be possible to omit the aqueous work-up, either by using filtration to collect the salt that has formed in the reaction and subjecting the collected salt to purification, or by furnishing the reaction mixture directly to purification.

Resist compositions prepared using the basic compounds having a benzimidazole skeleton and a polar functional group according to the invention are endowed with an excellent resolution and an excellent focus margin, and are thus useful in microfabrication using electron beams or deep-UV light. The addition of such compounds imparts significant effects in KrF resists, ArF resists, $F_2$ resists and EB resists. Such resists are highly suitable as micropatterning materials in the manufacture of VLSI chips.

EXAMPLES

Examples and comparative examples are given below by way of illustration, and not by way of limitation.

Basic compounds of the invention were synthesized by the procedure below.

Synthesis Example 1

Synthesis of 2-(1H-benzimidazol-1-yl)ethyl acetate (Amine 2)

A mixture of 118 g of benzimidazole, 48.5 g of ethylene oxide, and 400 g of N,N-dimethylacetamide was heated and stirred in an autoclave at 100° C. for 16 hours. The solvent was distilled off in vacuo, yielding crude 2-(1H-benzimidazol-1-yl)ethanol.

To a mixture of the crude 2-(1H-benzimidazol-1-yl)-ethanol and 500 g of pyridine, 122 g of acetic anhydride was added dropwise. In a nitrogen atmosphere, the reaction mixture was stirred at 20° C. for 10 hours. The reaction mixture was subjected to conventional aqueous work-up and then purified by vacuum distillation, obtaining 165 g of 2-(1H-benzimidazol-1-yl)ethyl acetate (boiling point 145° C./27 Pa, yield 87%).

IR (thin film): ν=3089, 3056, 2954, 1741, 1616, 1496, 1459, 1442, 1369, 1332, 1288, 1232, 1207, 1049, 767, 746 $cm^{-1}$ $^{1}$H-NMR (600 MHz in $CDCl_3$): δ=2.00 (3H, s), 4.37–4.43 (4H, m), 7.26–7.33 (2H, m), 7.40 (1H, br. d, J=7.6 Hz), 7.81 (1H, br. d, J=7.6 Hz), 7.92 (1H, s)

Amine 2

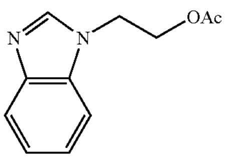

Synthesis Example 2

Synthesis of 2-(2-phenyl-1H-benzimidazol-1-yl)ethyl acetate (Amine 4)

The procedure of Synthesis Example 1 was repeated aside from using an equimolar amount of 2-phenylbenzimidazole instead of benzimidazole and purifying by column chromatography. There was synthesized 2-(2-phenyl-1H-benzimidazol-1-yl)ethyl acetate (yield 80%).

IR (thin film): ν=2968, 2960, 1729, 1612, 1523, 1473, 1457, 1448, 1436, 1388, 1365, 1355, 1330, 1284, 1272, 1247, 1228, 1166, 1122, 1076, 1047, 1024, 917, 775, 748, 698 $cm^{-1}$ $^1$H-NMR (600 MHz in $CDCl_3$): δ=1.86 (3H, s), 4.35 (2H, t, J=5.7 Hz), 4.51 (2H, t, J=5.7 Hz), 7.31–7.34 (2H, m), 7.46 (1H, m), 7.51–7.54 (3H, m), 7.73–7.74 (2H, m), 7.83 (1H, m)

Amine 4

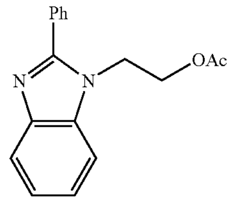

Synthesis Example 3

Synthesis of 3-(1H-benzimidazol-1-yl)propyl acetate (Amine 5)

In a nitrogen atmosphere, a mixture of 118 g of benzimidazole, 181 g of 3-bromopropyl acetate, 111 g of triethylamine, 2 g of sodium iodide, and 500 g of N,N-dimethylformamide was heated and stirred at 80° C. for 16 hours. The reaction mixture was subjected to conventional aqueous work-up and then purified by column chromatography, obtaining 3-(1H-benzimidazol-1-yl)propyl acetate (yield 70%).

Amine 5

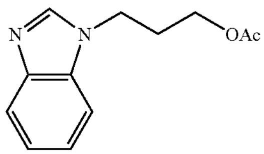

Synthesis Example 4

Synthesis of 2-(1H-benzimidazol-1-yl)ethyl methoxyacetate (Amine 16)

In a nitrogen atmosphere, a mixture of crude 2-(1H-benzimidazol-1-yl)ethanol as prepared in Synthesis Example 1, 156 g of methyl methoxyacetate, 3.0 g of sodium methoxide, and 200 g of diglyme was heated under reflux for 20 hours while distilling off the methanol formed during the reaction. The solvent was distilled off in vacuo. The reaction mixture was subjected to conventional aqueous work-up and then purified by column chromatography, obtaining 2-(1H-benzimidazol-1-yl)ethyl methoxyacetate (yield 65%).

Amine 16

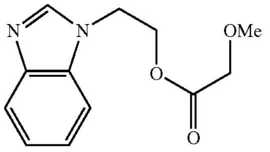

Synthesis Example 5

Synthesis of methyl 3-(2-phenyl-1H-benzimidazol-1-yl)-propionate (Amine 26)

A mixture of 194 g of 2-phenylbenzimidazole, 103 g of methyl acrylate and 500 g of methanol was heated and stirred at 60° C. for 100 hours. The solvent was distilled off in vacuo, followed by purification by column chromatography. There was obtained methyl 3-(2-phenyl-1H-benzimidazol-1-yl)-propionate (yield 60%).

Amine 26

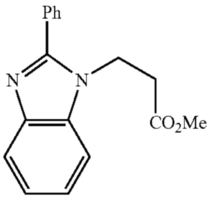

Synthesis Example 6

Synthesis of ethyl 4-(1H-benzimidazol-1-yl)butyrate (Amine 29)

The procedure of Synthesis Example 3 was repeated aside from using an equimolar amount of ethyl 4-bromobutyrate instead of 3-bromopropyl acetate. There was synthesized ethyl 4-(1H-benzimidazol-1-yl)butyrate (yield 82%).

Amine 29

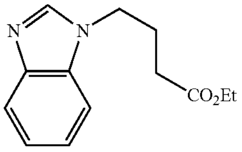

Synthesis Example 7

Synthesis of 1-[2-[(2-methoxyethoxy)methoxy]ethyl]-1H-benzimidazole (Amine 34)

The procedure of Synthesis Example 3 was repeated aside from using an equimolar amount of 1-bromo-2-[(2-methoxyethoxy)methoxy]ethane instead of 3-bromopropyl acetate. There was synthesized 1-[2-[(2-methoxyethoxy)methoxy]ethyl]-1H-benzimidazole (yield 74%).

Amine 34

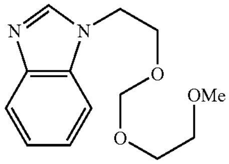

Synthesis Example 8

Synthesis of 1-[2-(1-ethoxyethoxy)ethyl]-1H-benzimidazole (Amine 38)

The procedure of Synthesis Example 3 was repeated aside from using an equimolar amount of 2-bromo-1-(1-ethoxyethoxy)ethane instead of 3-bromopropyl acetate. There was synthesized 1-[2-(1-ethoxyethoxy)ethyl]-1H-benzimidazole (yield 55%).

Amine 38

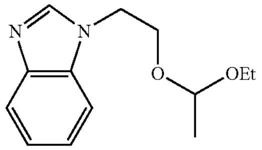

Synthesis Example 9

Synthesis of 1-[(2,2-dimethyl-1,3-dioxolan-4-yl)methyl]-1H-benzimidazole (Amine 54)

The procedure of Synthesis Example 3 was repeated aside from using an equimolar amount of 4-bromomethyl-2,2-dimethyl-1,3-dioxolane instead of 3-bromopropyl acetate. There was synthesized 1-[(2,2-dimethyl-1,3-dioxolan-4-yl)-methyl]-1H-benzimidazole (yield 80%).

Amine 54

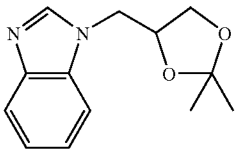

Synthesis Example 10

Synthesis of 1-[2-(1,3-dioxolan-2-yl)ethyl]-1H-benzimidazole (Amine 61)

The procedure of Synthesis Example 3 was repeated aside from using an equimolar amount of 2-(2-bromoethyl)-1,3-dioxolane instead of 3-bromopropyl acetate. There was synthesized 1-[2-(1,3-dioxolan-2-yl)ethyl]-1H-benzimidazole (yield 78%).

Amine 61

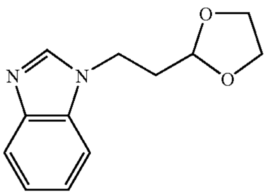

Synthesis Example 11

Synthesis of 4-(1H-benzimidazol-1-yl)butyronitrile (Amine 64)

The procedure of Synthesis Example 3 was repeated aside from using an equimolar amount of 4-bromobutyronitrile instead of 3-bromopropyl acetate. There was synthesized 4-(1H-benzimidazol-1-yl)butyronitrile (yield 83%).

Amine 64

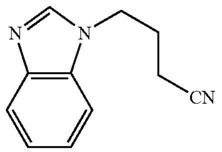

Resist Evaluation Examples:

In each example, a resist solution was prepared by dissolving a polymer, a photoacid generator, a base, a dissolution inhibitor and a crosslinking agent in a 70:30 by weight solvent mixture of propylene glycol monomethyl ether acetate (PGMEA) and ethyl lactate (EL), then filtering the solution using a Teflon® filter having a pore size of 0.1 μm.

The resulting resist solution was spin-coated onto a silicon wafer substrate on which had been formed a 55 nm thick film of DUV-30 (Nissan Chemical Industries, Ltd.) to hold the reflectance to KrF light (248 nm) to less than 1%, then baked at 100° C. for 90 seconds on a hot plate, giving a resist film having a thickness of 550 nm.

The resist film was exposed using an excimer laser stepper (NSR-S202A, manufactured by Nikon Corporation; NA=0.6; σ=0.75; ⅔ annular illumination) while varying the exposure dose and focus. Immediately after exposure, the resist was baked at 110° C. for 90 seconds, then developed for 60 seconds with a 2.38% solution of tetramethylammonium hydroxide in water, giving a resist pattern.

The resulting resist patterns were evaluated as described below. The results are shown in the following tables.

Method of Evaluation:

An optimal exposure dose (Eop) was the exposure which provided a 1:1 resolution of 0.16 μm lines and spaces. A focus margin was determined at the optimal exposure dose (Eop). The focus margin was defined as the absence of pattern film thickness loss and as having a size of not more than 0.16 μm±10%.

TABLE 1

Examples of Invention

| | Polymer (pbw) | Photoacid generator (pbw) | Base (pbw) | Dissolution inhibitor/ Crosslinker (pbw) | Sensitivity (mJ/cm$^2$) | Focus margin (μm) |
|---|---|---|---|---|---|---|
| Example | Polymer5 (100) | PAG3 (2) | Amine2 (0.12) | — | 38 | 1.1 |
| | Polymer5 (100) | PAG3 (2) | Amine4 (0.17) | — | 39 | 1.0 |
| | Polymer5 (100) | PAG3 (2) | Amine5 (0.12) | — | 41 | 0.9 |
| | Polymer5 (100) | PAG3 (2) | Amine16 (0.14) | — | 42 | 1.1 |
| | Polymer5 (100) | PAG3 (2) | Amine26 (0.17) | — | 39 | 1.0 |
| | Polymer5 (100) | PAG3 (2) | Amine29 (0.12) | — | 41 | 1.2 |
| | Polymer5 (100) | PAG3 (2) | Amine34 (0.14) | — | 40 | 0.9 |
| | Polymer5 (100) | PAG3 (2) | Amine38 (0.14) | — | 41 | 1.1 |

TABLE 1-continued

| Examples of Invention | | | | | |
|---|---|---|---|---|---|
| Polymer (pbw) | Photoacid generator (pbw) | Base (pbw) | Dissolution inhibitor/ Crosslinker (pbw) | Sensitivity ($mJ/cm^2$) | Focus margin (μm) |
| Polymer5 (100) | PAG3 (2) | Amine54 (0.12) | — | 40 | 1.0 |
| Polymer5 (100) | PAG3 (2) | Amine61 (0.14) | — | 39 | 1.0 |
| Polymer5 (100) | PAG3 (2) | Amine64 (0.10) | — | 38 | 1.2 |
| Polymer1 (100) | PAG5 (2) | Amine2 (0.12) | — | 45 | 0.9 |
| Polymer2 (100) | PAG5 (2) | Amine2 (0.12) | — | 49 | 0.9 |
| Polymer3 (100) | PAG5 (2) | Amine2 (0.12) | — | 47 | 1.1 |
| Polymer3 (100) | PAG4 (2) | Amine2 (0.12) | — | 47 | 1.0 |
| Polymer4 (100) | PAG2 (2) | Amine2 (0.12) | Crosslinker (15) | 31 | 0.8 |
| Polymer6 (100) | PAG1 (2) | Amine2 (0.12) | — | 45 | 0.9 |

TABLE 1-continued

| Examples of Invention | | | | | |
|---|---|---|---|---|---|
| Polymer (pbw) | Photoacid generator (pbw) | Base (pbw) | Dissolution inhibitor/ Crosslinker (pbw) | Sensitivity ($mJ/cm^2$) | Focus margin (μm) |
| Polymer7 (100) | PAG1 (2) | Amine2 (0.12) | — | 47 | 1.0 |
| Polymer8 (100) | PAG1 (2) | Amine2 (0.12) | — | 42 | 0.9 |
| Polymer9 (100) | PAG1 (2) | Amine2 (0.12) | — | 39 | 0.8 |
| Polymer10 (100) | PAG1 (2) | Amine2 (0.12) | — | 46 | 0.9 |
| Polymer11 (100) | PAG1 (2) | Amine2 (0.12) | — | 42 | 0.9 |
| Polymer12 (100) | PAG4 (2) | Amine2 (0.12) | — | 46 | 0.8 |
| Polymer13 (100) | PAG1 (2) | Amine2 (0.12) | — | 45 | 0.9 |
| Polymer5 (100) | PAG2 (2) | Amine2 (0.12) | DRI (20) | 30 | 1.0 |

TABLE 2

| Comparative Examples of Invention | | | | | | |
|---|---|---|---|---|---|---|
| | Polymer (pbw) | Photoacid generator (pbw) | Base (pbw) | Dissolution inhibitor/ Crosslinker (pbw) | Sensitivity ($mJ/cm^2$) | Focus margin (μm) |
| Comparative Example | Polymer5 (100) | PAG2 (2) | — | — | 8 | 0.2 |
| | Polymer5 (100) | PAG2 (2) | 1,8-bis(dimethylamino)-naphthalene (0.2) | — | 35 | 0.4 |
| | Polymer5 (100) | PAG2 (2) | DBN (0.1) | — | 34 | 0.4 |
| | Polymer5 (100) | PAG2 (2) | DBU (0.1) | — | 32 | 0.5 |
| | Polymer1 (100) | PAG5 (2) | DBN (0.1) | — | 52 | 0.2 |
| | Polymer2 (100) | PAG5 (2) | DBN (0.1) | — | 62 | 0.5 |
| | Polymer3 (100) | PAG5 (2) | DBN (0.1) | — | 51 | 0.3 |
| | Polymer3 (100) | PAG4 (2) | DBN (0.1) | — | 51 | 0.2 |
| | Polymer4 (100) | PAG2 (2) | DBN (0.1) | Crosslinker1 (15) | 33 | 0.3 |
| | Polymer6 (100) | PAG1 (2) | DBN (0.1) | — | 46 | 0.6 |
| | Polymer7 (100) | PAG1 (2) | DBN (0.1) | — | 48 | 0.6 |
| | Polymer8 (100) | PAG1 (2) | DBN (0.1) | — | 42 | 0.6 |
| | Polymer9 (100) | PAG1 (2) | DBN (0.1) | — | 45 | 0.4 |
| | Polymer10 (100) | PAG1 (2) | DBN (0.1) | — | 48 | 0.3 |
| | Polymer11 (100) | PAG1 (2) | DBN (0.1) | — | 42 | 0.4 |
| | Polymer12 (100) | PAG4 (2) | DBN (0.1) | — | 46 | 0.2 |
| | Polymer13 (100) | PAG1 (2) | DBN (0.1) | — | 45 | 0.3 |
| | Polymer5 (100) | PAG2 (2) | DBN (0.1) | DRI1 (20) | 29 | 0.3 |

1,8-bis(dimethylamino)naphthalene
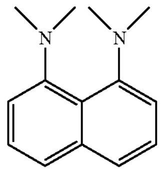
DBN: 1,5-diazabicyclo[4.3.0]-5-nonene
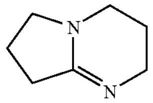
DBU: 1,8-diazabicyclo[5.4.0]-7-undecene
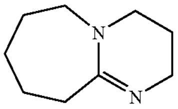
Polymer 1
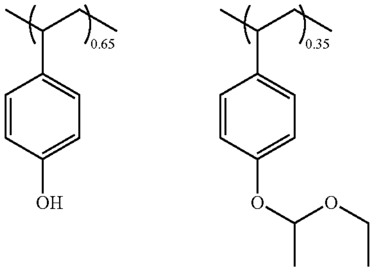
Mw 10,000
Mw/Mn 1.10
Polymer 2
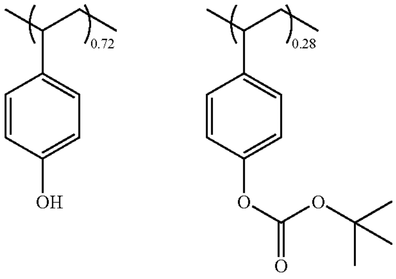
Mw 10,000
Mw/Mn 1.10
-continued
Polymer 3
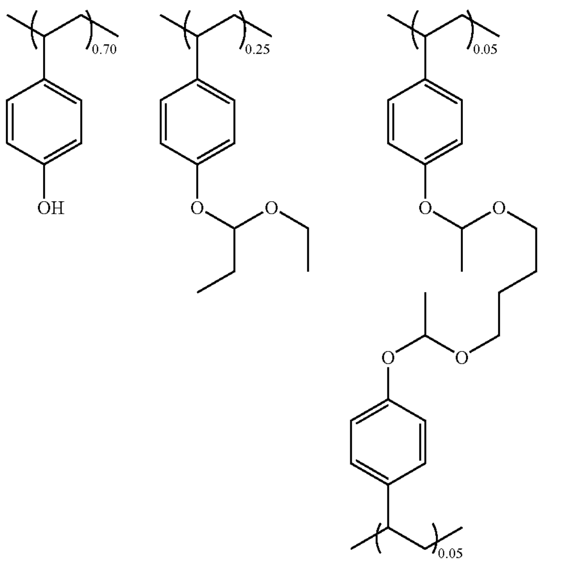
Mw 16,000
Mw/Mn 1.60
Polymer 4
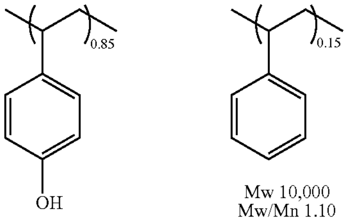
Mw 10,000
Mw/Mn 1.10
Polymer 5
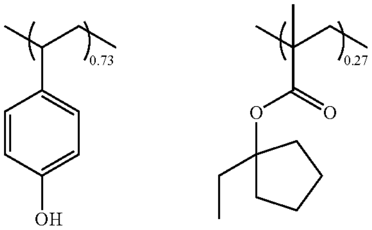
Mw 12,000
Mw/Mn 1.60
Polymer 6
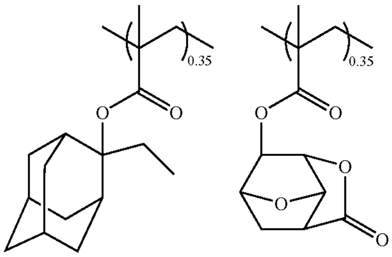

-continued
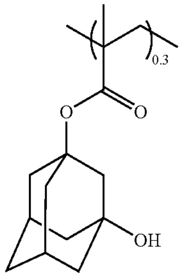
Mw 8,000
Mw/Mn 1.90
Polymer 7
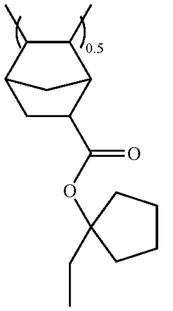
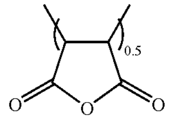
Mw 10,000
Mw/Mn 1.50
Polymer 8
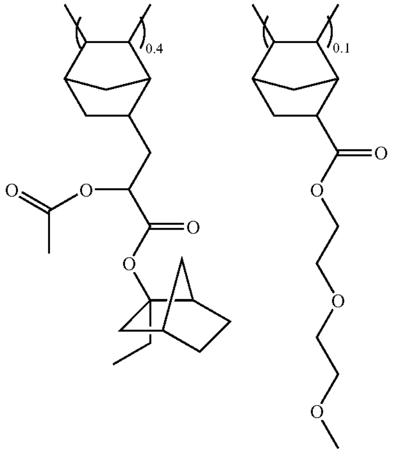
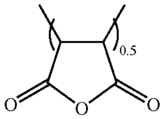
Mw 11,000
Mw/Mn 1.58
Polymer 9
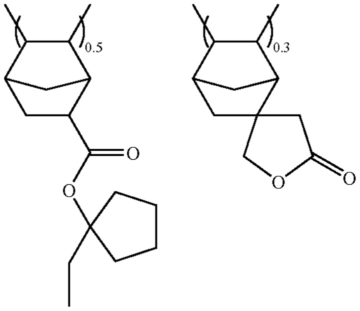
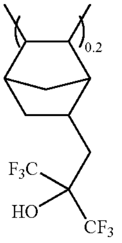
Mw 8,000
Mw/Mn 2.0
-continued
Polymer 10
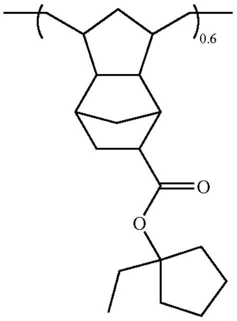
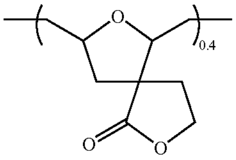
Mw 13,000
Mw/Mn 1.20
Polymer 11
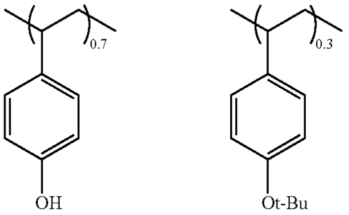
Mw 8,000
Mw/Mn 1.10
Polymer 12
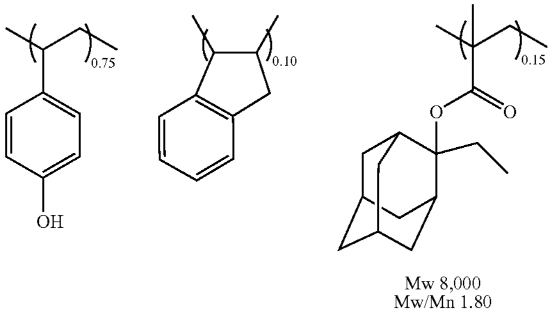
Mw 8,000
Mw/Mn 1.80
Polymer 13
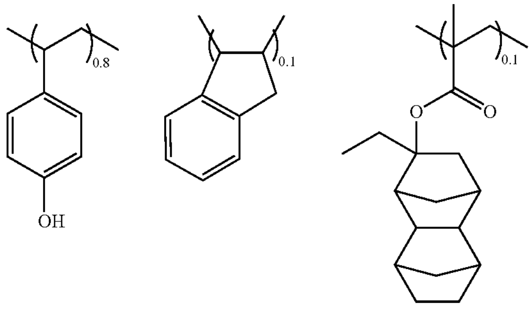
Mw 8,000
Mw/Mn 1.80
PAG1
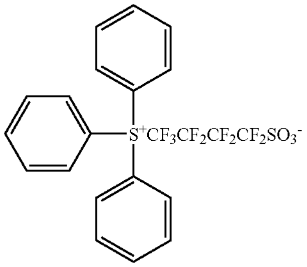

-continued
PAG2
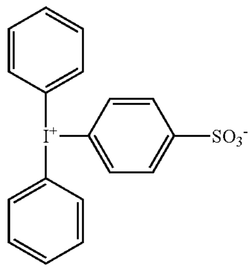
PAG3
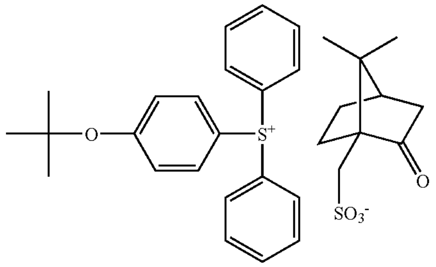
PAG4
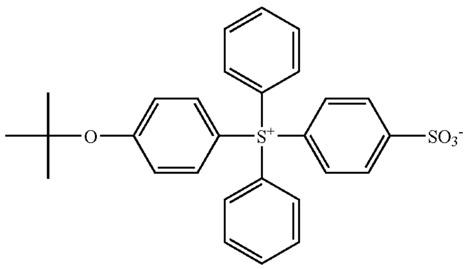
PAG5
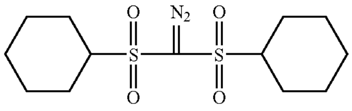
DRI 1
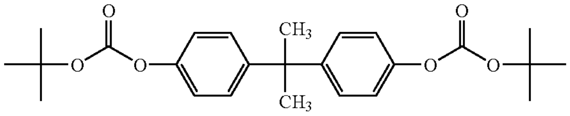
Crosslinker 1
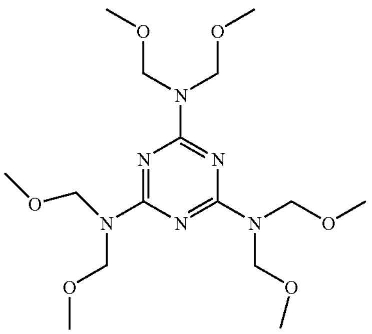
The invention claimed is:
1. A positive-working resist composition comprising:
(A) at least one basic compound having a benzimidazole skeleton and a polar functional group, represented by the general formulae (2) to (7):
(2)
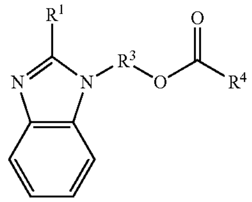
(3)
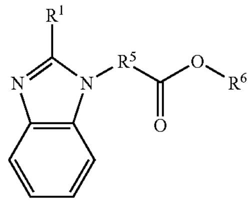
(4)
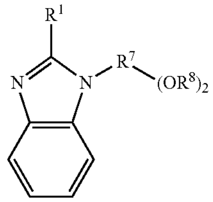
(5)
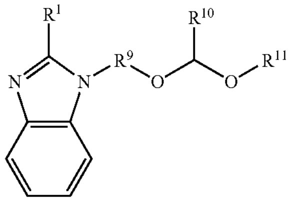
(6)
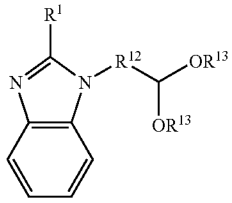
(7)
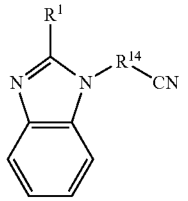

wherein $R^1$ is a hydrogen atom, a straight, branched or cyclic alkyl group of 1 to 10 carbon atoms, an aryl group of 6 to 10 carbon atoms, or an aralkyl group of 7 to 10 carbon atoms;

$R^3$, $R^5$, $R^9$, $R^{12}$ and $R^{14}$ are each independently a straight, branched or cyclic alkylene group of 1 to 10 carbon atoms;

$R^4$ is a hydrogen atom or an alkyl group of 1 to 15 carbon atoms which may contain at least one group selected from among hydroxyl, carbonyl, ester, ether, sulfide, carbonate, cyano and acetal groups;

$R^6$ is an alkyl group of 1 to 15 carbon atoms which may contain at least one group selected from among hydroxyl, carbonyl, ester, ether, sulfide, carbonate, cyano and acetal groups;

$R^7$ is a trivalent, straight, branched or cyclic hydrocarbon group of 2 to 10 carbon atoms;

$R^8$ is each independently an acyl group of 1 to 10 carbon atoms which may contain at least one ester or ether group, or two $R^8$ may bond together to form a cyclic carbonate or cyclic acetal;

$R^{10}$ is a hydrogen atom or a straight, branched or cyclic alkyl group of 1 to 10 carbon atoms;

$R^{11}$ is a straight, branched or cyclic alkyl group of 1 to 10 carbon atoms which may contain at least one group selected from among ether, sulfide and acetal groups, or $R^{10}$ and $R^{11}$ may bond together to form a ring;

$R^{13}$ is a straight, branched or cyclic alkyl group of 1 to 10 carbon atoms, or two $R^{13}$ may bond together to form a ring;

(B) an organic solvent;

(C) a base resin having an acid labile group-protected acidic functional group which is alkali-insoluble or substantially alkali-insoluble, but becomes alkali-soluble when the acid labile group is eliminated; and (D) a photoacid generator.

2. The positive resist composition of claim 1 which further comprises (E) a dissolution inhibitor.

3. A negative-working resist composition comprising:

(A) at least one basic compound having a benzimidazole skeleton and a polar functional group, represented by the general formula (1):

(1)

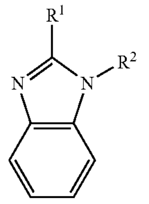

wherein $R^1$ is a hydrogen atom, a straight, branched, or cyclic alkyl group of 1 to 10 carbon atoms, an aryl group of 6 to 10 carbon atoms, or an aralkyl group of 7 to 10 carbon atoms; and $R^2$ is a polar functional group-bearing straight, branched, or cyclic alkyl group of 1 to 20 carbon atoms wherein said alkyl group contains as the polar functional group at least one group selected from among ester, acetal, and cyano groups, and optionally at least one group selected from among hydroxyl, carbonyl, ether, sulfide, and carbonate groups;

(B) an organic solvent;

(C') a base resin which is alkali-soluble, but becomes substantially alkali-insoluble when crosslinked with a crosslinking agent;

(D) a photoacid generator; and (F) a crosslinking agent which induces crosslinkage under the action of an acid.

4. A patterning process comprising the steps of:

(1) applying the positive resist composition of claim 2 onto a substrate;

(2) heat treating the applied resist, then exposing the heat-treated resist through a photomask to high-energy radiation having a wavelength of at most 300 nm or an electron beam; and (3) heat treating the exposed resist, then developing the resist with a liquid developer.

5. A patterning process comprising the steps of:

(1) applying the negative resist composition of claim 3 onto a substrate;

(2) heat treating the applied resist, then exposing the heat-treated resist through a photomask to high-energy radiation having a wavelength of at most 300 nm or an electron beam; and (3) heat treating the exposed resist, then developing the resist with a liquid developer.

6. The resist composition of claim 1 wherein the basic compound is at least one selected from the group consisting of compounds represented by the following general formulae:

(2)

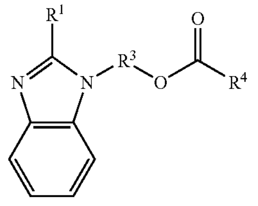

(4)

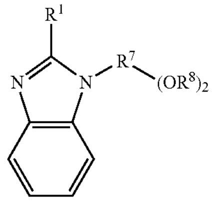

(5)

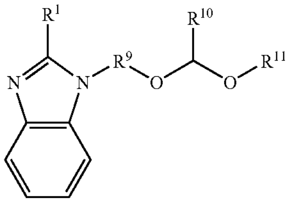

(6)

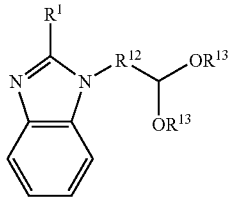

wherein $R^1$ is a hydrogen atom, methyl group or phenyl group; $R^3$, $R^9$, and $R^{12}$ are each independently a straight, branched or cyclic alkylene group of 1 to 10 carbon atoms;

$R^4$ is a hydrogen atom or an alkyl group of 1 to 15 carbon atoms which may contain at least one group selected from among hydroxyl, carbonyl, ester, ether, sulfide, carbonate, cyano and acetal groups; $R^7$ is a trivalent, straight, branched or cyclic hydrocarbon group of 2 to 10 carbon atoms; $R^8$ is each independently an acyl group of 1 to 10 carbon atoms which may contain at least one ester or ether group, or two $R^8$ may bond together to form a cyclic carbonate or cyclic acetal; $R^{10}$ is a hydrogen atom or a straight, branched or cyclic alkyl group of 1 to 10 carbon atoms; $R^{11}$ is a straight, branched or cyclic alkyl group of 1 to 10 carbon atoms which may contain at least one group selected from among ether, sulfide and acetal groups, or $R^{10}$ and $R^{11}$ may bond together to form a ring; and $R^{13}$ is a straight, branched or cyclic alkyl group of 1 to 10 carbon atoms, or two $R^{13}$ may bond together to form a ring.

* * * * *